United States Patent
Hu et al.

(10) Patent No.: US 9,518,981 B2
(45) Date of Patent: Dec. 13, 2016

(54) MODIFIED NUCLEIC ACID BINDING CYANINE DYES FOR THE DETECTION OF REACTIVE OXYGEN SPECIES

(71) Applicant: LIFE TECHNOLOGIES CORPORATION, Carlsbad, CA (US)

(72) Inventors: Yi-Zhen Hu, Eugene, OR (US); Aimei Chen, Eugene, OR (US); Hee Chol Kang, Eugene, OR (US); Kyle Gee, Springfield, OR (US); Bhaskar Mandavilli, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/384,843

(22) PCT Filed: Feb. 26, 2013

(86) PCT No.: PCT/US2013/027805
§ 371 (c)(1),
(2) Date: Sep. 12, 2014

(87) PCT Pub. No.: WO2013/148038
PCT Pub. Date: Oct. 3, 2013

(65) Prior Publication Data
US 2015/0079622 A1     Mar. 19, 2015

Related U.S. Application Data

(60) Provisional application No. 61/617,862, filed on Mar. 30, 2012.

(51) Int. Cl.
| | | |
|---|---|---|
| C07D 215/00 | (2006.01) |
| G01N 33/52 | (2006.01) |
| C09B 23/02 | (2006.01) |
| C09B 23/04 | (2006.01) |
| C09B 23/06 | (2006.01) |
| G01N 33/84 | (2006.01) |
| C07D 417/06 | (2006.01) |

(52) U.S. Cl.
CPC ............ *G01N 33/52* (2013.01); *C07D 417/06* (2013.01); *C09B 23/02* (2013.01); *C09B 23/04* (2013.01); *C09B 23/06* (2013.01); *G01N 33/84* (2013.01)

(58) Field of Classification Search
None
See application file for complete search history.

(56) References Cited

FOREIGN PATENT DOCUMENTS

| CN | 1253507 | 5/2000 |
| CN | 101522815 | 9/2009 |
| CN | 102344794 | 2/2012 |
| WO | WO-2009/121055 | 10/2009 |
| WO | WO-2012/061403 | 5/2012 |

OTHER PUBLICATIONS

CAPLUS 1965:52169.*
PCT/US2013/027805, , "International Preliminary Report on Patentability and Written Opinion mailed on Oct. 1, 2014", Oct. 1, 2014, 6 pages.
PCT/US2013/027805, , "International Search Report and Written Opinion", Apr. 26, 2013, 9 pgs.

* cited by examiner

Primary Examiner — Heidi Reese

(57) ABSTRACT

Disclosed herein are compounds, compositions, methods, and kits for detecting reactive oxygen species (ROS) by conventional fluorescence microscopy, fluorescence spectroscopy, flow cytometry, and/or high content imaging. The compounds disclosed herein are novel reduced nucleic acid binding cyanine dyes, which dyes are probes for detecting ROS and measuring oxidative stress in cells either in vitro and/or in vivo. Also described herein are processes for preparing novel reduced dyes, i.e., ROS probes, for use in the disclosed compositions, methods and kits.

19 Claims, 10 Drawing Sheets

MODIFIED NUCLEIC ACID BINDING CYANINE DYES FOR THE DETECTION OF REACTIVE OXYGEN SPECIES

CROSS-REFERENCE TO RELATED APPLICATIONS

This application is a national stage entry of PCT/US2013/027805, filed Feb. 26, 2013 and claims the benefit of priority to U.S. Provisional Application Ser. No. 61/617,862, filed Mar. 30, 2012, which is herein incorporated by reference in its entirety.

FIELD

The present invention relates to probes useful for detecting reactive oxygen species (ROS), in particular reduced nucleic acid binding cyanine dye probes, as well as uses of such probes in vitro or in vivo.

BACKGROUND

Oxidative stress results from an imbalance between the production of reactive oxygen species (ROS) and the ability of cells to scavenge such species. Oxidative stress can be caused by many different pathways, intrinsic and extrinsic, mediated either by mitochondrial respiration or by membrane-bound NADPH oxidases. ROS play an important role in the progression of several diseases including, but not limited to, inflammation, atherosclerosis, aging and age-related degenerative disorders. Probes that can detect ROS in serum samples, live tissue explants, cell cultures, and in vivo have potential uses for medical diagnostics and research tools for the diagnoses of diseases characterized by increased ROS production.

Imaging enables multiplex analysis, localization and quantitation of different parameters related to cytotoxicity and cell death in the same cell. Thus, detection of ROS by conventional fluorescence microscopy, fluorescence spectroscopy, flow cytometry, and/or high content imaging is likely to be advantageous over other techniques. Fluorescent sensors for superoxide and the hydroxyl radical, such as dihydroethidium (DHE), have been used as ROS probes. However, DHE has limited applicability due to its spontaneous auto-oxidation, rapid photobleaching, high toxicity, and multiple reaction products with ROS. Furthermore, the lower emission wavelength of DHE makes its use in vivo problematic. Dihydrorhodamine (DHR), another reduced dye that has been investigated for detection of ROS, suffers from high rates of oxidation, thereby limiting its applications. Reduced cyanine dyes developed thus far as probes for ROS, which are based on Cy3/Cy5/Cy7, suffer to varying degrees from solubility problems and/or from auto-oxidation. Sulfonate ester-based dyes have also been investigated as ROS probes. These probes, which typically require multistep synthesis procedures that are time-consuming and expensive, undergo rapid hydrolysis thereby limiting their application.

Thus, there exists a need for probes to detect ROS, amenable for use in vitro or in vivo, that do not suffer from the limitations of prior art ROS probes, such as their tendency to undergo spontaneous auto-oxidation catalyzed by oxygen and/or light with concomitant production of high levels of background fluorescence.

SUMMARY

Described herein are reduced dye compounds, compositions, methods, and kits for detecting reactive oxygen species (ROS) by, for example, conventional fluorescence microscopy, fluorescence spectroscopy, flow cytometry, and/or high content imaging. The reduced dye compounds disclosed herein are novel reduced nucleic acid binding cyanine dyes, which dyes are probes for detecting ROS and measuring oxidative stress in cells in vitro or in vivo. These probes are useful in multiplex applications with other live-cell dyes, making them useful to measure multiple biomarkers of cytotoxicity and cell death, and may be used to evaluate ROS generated by various agents including, but not limited to, lipopolysaccharide, menadione, angiotensin II, nefazodone, ionomycin, and glutamate in a variety of live cell models.

The reduced nucleic acid binding cyanine dyes disclosed herein, which are generally membrane permeable and may therefore accumulate in cells, are unable to bind nucleic acid and exhibit little or no fluorescence compared to the corresponding oxidized dyes. Upon intracellular reaction with, i.e., detection of, ROS, the reduced dyes disclosed herein are oxidized thereby affording a high-affinity nucleic acid binding cyanine dye with substantial fluorescence intensity upon exposure to light of sufficient wavelength. FIG. 1 shows a schematic illustration of intracellular ROS detection with a reduced nucleic acid binding cyanine dye using Thiazole Orange (TO) as an example. The reduced Thiazole Orange (Reduced TO) crosses the cell membrane to enter the cell, where it can be oxidized by ROS to release the high-affinity nucleic acid binding dye (TO) and emit a bright green fluorescence. The reduced dyes disclosed herein, in combination with, for example, probes for mitochondrial membrane potential, plasma membrane permeability, and/or caspase activation, may also be used to differentiate hepatotoxic compounds from non-toxic compounds. Also described herein are processes for preparing novel reduced dyes, i.e., ROS probes, for use in the disclosed compositions, methods and kits of the present invention.

In certain embodiments, novel reduced dye compounds (i.e., ROS probes) having structural formula (I) are provided:

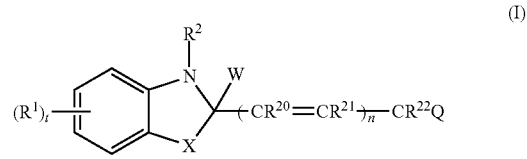

wherein each $R^1$, which may be the same or different, is independently H; $C_1$-$C_6$ alkyl; trifluoromethyl; halogen; —$OR^8$, —$SR^8$, or —($NR^8R^9$), where $R^8$ and $R^9$, which may be the same or different, are independently H; $C_1$-$C_6$ alkyl; or 1-2 alicyclic hetroalicyclic, aromatic or heteroaromatic rings having a total of 3-16 ring atoms, wherein the heteroatoms are O, N, or S; or $R^8$ and $R^9$ taken in combination are —($CH_2$)$_2$-L-($CH_2$)$_2$— where L is a single bond; —$CH_2$—; —O—; or —$NR^{10}$, where $R^{10}$ is H or a $C_1$-$C_6$ alkyl;

t is 1, 2, 3 or 4;

$R^2$ is a substituted or unsubstituted $C_1$-$C_6$ alkyl;

X is O; S; Se; $NR^{15}$, where $R^{15}$ is H or a $C_1$-$C_6$ alkyl; or $CR^{16}R^{17}$, where $R^{16}$ and $R^{17}$, which may be the same or different, are independently H or $C_1$-$C_6$ alkyl, or the carbons of $R^{16}$ and $R^{17}$ taken in combination complete a five- or six-membered saturated ring;

Q has the formula Q1 or Q2:

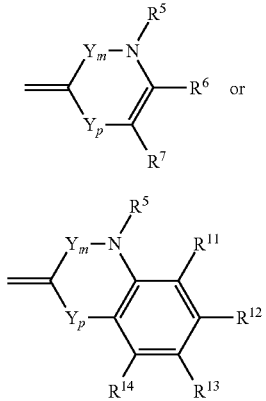

(Q1)

(Q2)

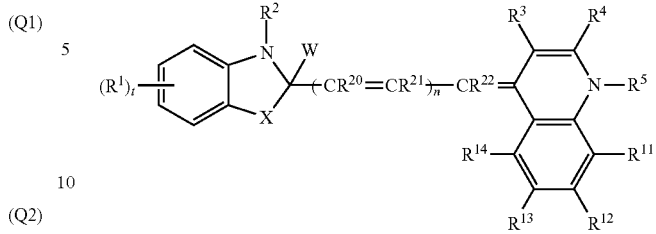

(II)

wherein

Y is —$CR^3$=$CR^4$—;

p and m are 0 or 1, such that p+m=1;

$R^5$ is a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; or an OMEGA;

$R^3$, $R^4$, $R^6$ and $R^7$, which may be the same or different, are each independently H; halogen; a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; —$OR^8$; —$SR^8$; —($NR^8R^9$), as defined previously; —$OSO_2R^{19}$, where $R^{19}$ is a $C_1$-$C_6$ alkyl, $C_1$-$C_6$ perfluoroalkyl, or aryl; or an OMEGA; or $R^6$ and $R^7$, taken in combination are —$(CH_2)_v$—, where v is 3 or 4, or $R^6$ and $R^7$ form a fused aromatic ring according to the formula Q2;

$R^{11}$, $R^{12}$, $R^{13}$ and $R^{14}$, which may be the same or different, are each independently H; a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; a halogen; an OMEGA; or —OH, —$OR^8$, —$SR^8$, or —($NR^8R^9$), as defined previously;

OMEGA is a saturated or unsaturated, substituted or unsubstituted, cyclic substituent that has a total of 2-16 ring carbon atoms in 1-2 alicyclic, heteroalicyclic, aromatic, or heteroaromatic rings, containing 1-4 heteroatoms wherein the heteroatoms are O, N, or S, that is unsubstituted or optionally substituted one or more times, independently, by halogen, alkyl, perfluoroalkyl, amino, alkylamino, dialkylamino, alkoxy or carboxyalkyl, having 1-6 carbons, and that is attached as $R^3$, $R^4$, $R^5$, $R^{11}$, $R^{12}$, $R^{13}$, or $R^{14}$ by a single bond, and, where more than one of $R^3$, $R^4$, $R^5$, $R^{11}$, $R^{12}$, $R^{13}$, and $R^{14}$ is an OMEGA, each OMEGA is optionally the same or different;

$R^{20}$, $R^{21}$ and $R^{22}$ are independently H, $C_1$-$C_6$ alkyl, $C_3$-$C_{10}$ cycloalkyl, aryl or heteroaryl;

W is H or D in either the R or S configuration; and n is 0, 1, 2, or 3.

In certain embodiments, novel reduced dye compounds (i.e., ROS probes) having structural formula (II) are provided:

wherein each $R^1$, which may be the same or different, is independently H; $C_1$-$C_6$ alkyl; trifluoromethyl; halogen; —$OR^8$, —$SR^8$, or —($NR^8R^9$), where $R^8$ and $R^9$, which may be the same or different, are independently H; $C_1$-$C_6$ alkyl; or 1-2 alicyclic hetroalicyclic, aromatic or heteroaromatic rings having a total of 3-16 ring atoms, wherein the heteroatoms are O, N, or S; or $R^8$ and $R^9$ taken in combination are —$(CH_2)_2$-L-$(CH_2)_2$— where L is a single bond; —$CH_2$—; —O—; or —$NR^{10}$, where $R^{10}$ is H or a $C_1$-$C_6$ alkyl;

t is 1, 2, 3 or 4;

$R^2$ is a substituted or unsubstituted $C_1$-$C_6$ alkyl;

$R^5$ is an alkyl, alkenyl, polyalkenyl, alkynyl or polyalkynyl group having 1-6 carbons; or an OMEGA;

$R^3$, $R^4$, $R^{11}$, $R^{12}$, $R^{13}$ and $R^{14}$ are each independently H; halogen; an alkyl, alkenyl, polyalkenyl, alkynyl or polyalkynyl group having 1-6 carbons; —$OR^8$; —$SR^8$; —($NR^8R^9$), as defined previously; —$OSO_2R^{19}$, where $R^{19}$ is a $C_1$-$C_6$ alkyl, $C_1$-$C_6$ perfluoroalkyl, or aryl; or an OMEGA;

OMEGA is a saturated or unsaturated, substituted or unsubstituted, cyclic substituent that has a total of 2-16 ring carbon atoms in 1-2 alicyclic, heteroalicyclic, aromatic, or heteroaromatic rings, containing 1-4 heteroatoms wherein the heteroatoms are O, N, or S, that is unsubstituted or optionally substituted one or more times, independently, by halogen, alkyl, perfluoroalkyl, amino, alkylamino, dialkylamino, alkoxy or carboxyalkyl, having 1-6 carbons, and that is attached as $R^3$, $R^4$, $R^5$, $R^{11}$, $R^{12}$, $R^{13}$, or $R^{14}$ by a single bond, and, where more than one of $R^3$, $R^4$, $R^5$, $R^{11}$, $R^{12}$, $R^{13}$, and $R^{14}$ is an OMEGA, each OMEGA is optionally the same or different;

X is O; S; Se; $NR^{15}$, where $R^{15}$ is H or a $C_1$-$C_6$ alkyl; or $CR^{16}R^{17}$, where $R^{16}$ and $R^{17}$, which may be the same or different, are independently H or $C_1$-$C_6$ alkyl, or the carbons of $R^{16}$ and $R^{17}$ taken in combination complete a five- or six-membered saturated ring;

$R^{20}$, $R^{21}$ and $R^{22}$ are independently H, $C_1$-$C_6$ alkyl, $C_3$-$C_{10}$ cycloalkyl, aryl or heteroaryl;

W is H or D in either the R or S configuration; and n is 0, 1, 2, or 3.

In certain embodiments, compositions for the detection of reactive oxygen species (ROS) are provided, the compositions comprising:

a) one or more of the reduced dye compounds described herein; and b) a carrier, wherein the reduced dye compounds are present in an amount effective to detect the presence of ROS upon reaction with the ROS.

In certain embodiments, methods are provided for detecting reactive oxygen species (ROS) in a sample, the methods comprising the steps of:

a) contacting the sample with an effective amount of one or more of the reduced dye compounds described herein or the compositions described herein; and b) determining if the reduced dye compound has been oxidized.

In certain embodiments, kits are provided for detecting reactive oxygen species (ROS) in a sample, the kits comprising:

a) one or more of the reduced dye compounds described herein or the compositions described herein; and b) one or more containers.

In certain embodiments, kits are provided for detecting reactive oxygen species (ROS) in a sample, the kits comprising:

a) one or more of the unreduced cyanine compounds described herein (e.g., compounds having structural formula (III) or (IV));

b) one or more reducing agents; and c) one or more containers.

In certain embodiments, the kits provided herein further comprise instructions for performing an assay for detecting one or more ROS in a sample. In certain embodiments, the kits provided herein are suitable for use with in vitro assays. In certain embodiments, the kits provided herein are suitable for use with in vivo assays. In certain embodiments, the kits provided herein further comprise instructions for preparing one or more reduced dye compounds.

In certain embodiments, processes are provided for preparing reduced dye compounds (i.e., ROS probes) of structural formula (I):

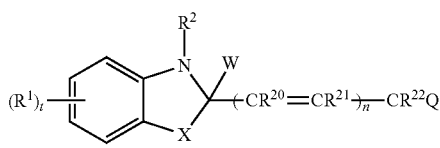
(I)

the process comprising:

a) reacting a cyanine compound having structural formula (III)

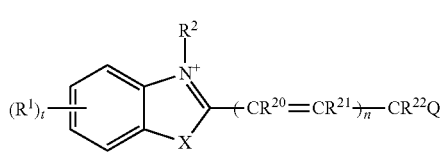
(III)

with a reducing agent, wherein:

Q, W, X, $R^1$, $R^2$, $R^{20}$, $R^{21}$, $R^{22}$, n, and t are as defined previously herein.

In certain embodiments, processes are provided for preparing reduced dye compounds (i.e., ROS probes) having structural formula (II):

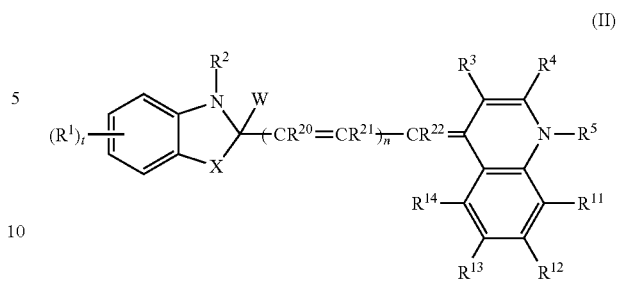
(II)

the process comprising:

a) reacting a cyanine compound having structural formula (IV):

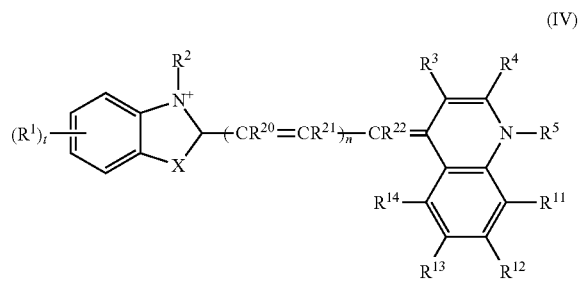
(IV)

with a reducing agent, wherein:

W, X, $R^1$, $R^2$, $R^3$, $R^4$, $R^5$, $R^{11}$, $R^{12}$, $R^{13}$, $R^{14}$, $R^{20}$, $R^{21}$, $R^{22}$, n, and t are as defined previously herein.

Other embodiments and illustrative aspects, features and advantages of the present invention will become apparent from the following detailed description. It should be understood, however, that the detailed description and the specific examples that follow, while indicating preferred embodiments of the invention, are given by way of illustration only. It is expected that various changes and modifications within the spirit and scope of the present invention will become apparent to those skilled in the art.

DETAILED DESCRIPTION

Figure 1:
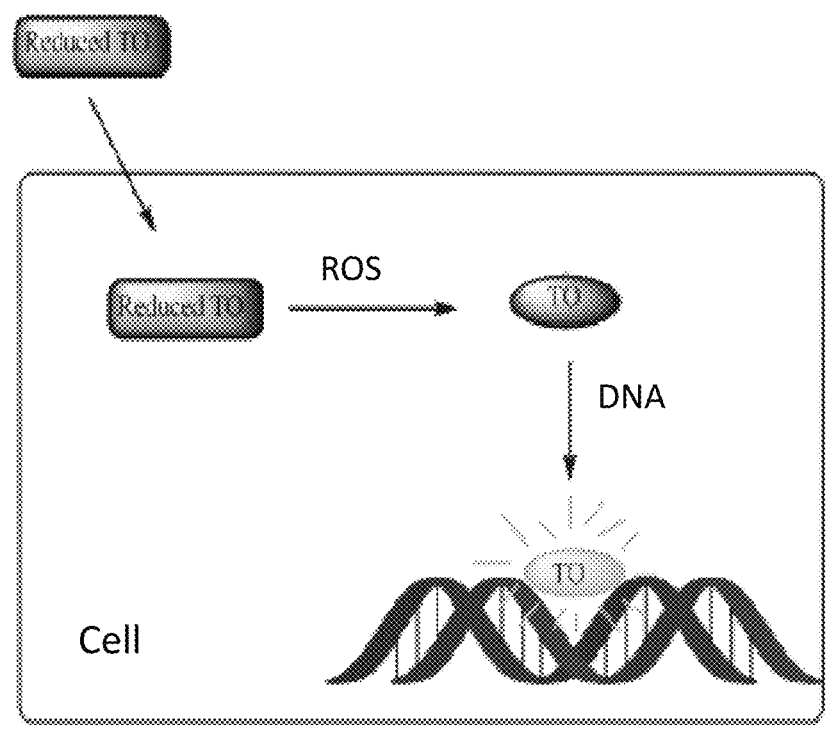
FIG. 1 shows a schematic illustration of intracellular ROS detection with a reduced nucleic acid binding cyanine dye, using Thiazole Orange (TO) as an example.

Disclosed herein are reduced dye compounds, compositions, methods, and kits for detecting reactive oxygen species (ROS) by conventional fluorescence microscopy, fluorescence spectroscopy, flow cytometry, and/or high content imaging. The reduced dye compounds disclosed herein are novel reduced nucleic acid binding dyes, which dyes are probes for detecting ROS and measuring oxidative stress in cells in vitro or in vivo. Also provided herein are processes for preparing the reduced dyes disclosed herein, i.e., ROS probes, for use in the compositions, methods and kits described herein.

The reduced dye compounds disclosed herein display enhanced stability to auto-oxidation, have tunable emission wavelengths, and nanomolar to millimolar sensitivity for ROS. Unexpectedly, unlike other prior art ROS probes, the reduced dye compounds disclosed herein also display resistance to formaldehyde fixation and detergent permeabilization. In addition, the reduced dye compounds disclosed herein may be used under more physiological conditions, such as in complete media; unlike other prior art ROS probes. Furthermore, there is no requirement for a post-staining washing step when using the reduced dye compounds disclosed herein, whereas other prior art ROS probes have such a requirement.

DEFINITIONS

To more clearly and concisely describe and point out the subject matter of the present disclosure, the following definitions are provided for specific terms, which are used in the following description and the appended claims. Throughout the specification, exemplification of specific terms should be considered as non-limiting examples.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a reduced dye" includes a plurality of dyes and reference to "a cell" includes a plurality of cells and the like. The phrase "and/or" denotes a shorthand way of indicating that the specific combination is contemplated in combination and separately, in the alternative. For illustration purposes, but not as a limitation, "X and/or Y" can mean "X" or "Y" or "X" and "Y".

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the above specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The section headings used herein are for organizational purposes only and are not to be construed as limiting the desired subject matter in any way. All literature cited in the specification, including but not limited to, patents, patent applications, articles, books and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure is related. The following terms are defined for purposes of the teachings as described herein.

As used herein, "reduced dye" or "reduced dye compound" refers to a dye molecule in which one or more π-bonds have been reduced, disrupting the extended π-conjugation, resulting in a molecule that exhibits negligible or no fluorescence.

As used herein, "nucleic acid binding cyanine dye" refers to a cyanine dye capable of binding to a nucleic acid to form a fluorescent dye-nucleic acid complex. A nucleic acid binding dye is typically non-fluorescent or weakly fluorescent by itself, but becomes highly fluorescent upon binding to nucleic acid.

As used herein, "cyanine dye" refers to closed-chain cyanine dyes, i.e., cyanine dyes having end groups that are cyclic moieties, wherein the cyclic moieties may be aromatic or non-aromatic and substituted or unsubstituted at one or more positions.

As used herein, "reduced dye," "reduced cyanine dye," "hydrocyanine," and "deuterocyanine" refer interchangeably and generally to a cyanine dye wherein the imminium cation has been reduced. "Deuterocyanine," as used herein, refers to a cyanine dye that has been reduced by a deuterated reducing agent thus incorporating deuterium into the reduced molecule. Examples of reduced imminium cations are shown below:

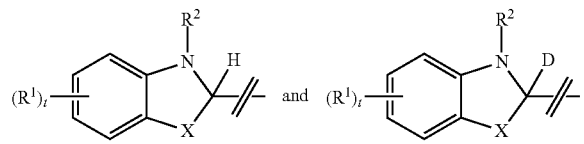

wherein $R^1$, $R^2$, X, and t are as defined previously herein.

As used herein, "reactive oxygen species" and "ROS" refer interchangeably to molecules or ions that contain oxygen ions, free radicals, peroxides, or combinations thereof. Reactive oxygen species may be organic or inorganic. Examples of reactive oxygen species include, but are not limited to, super oxides; free radicals, such as hydroxyl radicals and peroxyl radicals; peroxides, singlet oxygen, ozone, nitrogen monoxide; anions, such as hydroxyl anions and superoxide anions; hypochlorous acid; and peroxynitrites, as well as combinations of any such reactive oxygen species.

As used herein, "reducing agent" refers to a compound that is capable of donating a hydrogen or a deuterium to another molecule. Examples of reducing agents include, but are not limited to, metal salts, such as $LiAlH_4$, $NaBH_4$, $Zn(BH_4)_2$, compounds containing a $Sn^{2+}$ ion, sulfite compounds, diisobutyl aluminum hydride (DIBAH), oxalic acid, formic acid, ascorbic acid, phosphites, hypophosphate, hypophorphorous acid, dithiothreitol (DTT), and compounds containing the $Fe^{2+}$ ion. Any of these may have the hydrogen replaced by deuterium, for example, $NaBD_4$, $LiAlD_4$, $Zn(BD_4)_2$, etc.

As used herein, "membrane permeable" refers to a molecule that can enter a cell through passive diffusion.

As used herein, "alkylaryl" refers to an alkyl group substituted with an aryl group (e.g., an aromatic group or an heteroaromatic group).

As used herein, "alkyl" refers to a hydrocarbon that is optionally linear or branched, and may be fully saturated, mono- or polyunsaturated. Similarly, the alkyl portions of perfluoroalkyl, alkoxy, alkylthio, monoalkylamino, dialkylamino or alkylamido groups are optionally linear or branched, and may be fully saturated, mono- or polyunsaturated. In addition, the term "alkyl," as used herein, further includes one or more substitutions at one or more carbon atoms of the hydrocarbon chain fragment.

As used herein, "aryl" refers to an aromatic moiety having a single ring or multiple condensed rings each of which is optionally and independently substituted with H, halogen, cyano, azido, sulfonic acid, alkali or ammonium salt of sulfonic acid, carboxylic acid, biologically compatible salt of carboxylic acid, nitro, alkyl, perfluoroalkyl, alkoxy, alkylthio, amino, monoalkylamino, dialkylamino or alkylamido.

As used herein, "heteroaryl" refers to a 5- or 6-membered aromatic heterocycle that is optionally fused to an additional six-membered aromatic ring or to one 5- or 6-membered heteroaromatic ring, said heteroaromatic ring containing 1-3 heteroatoms that are selected from the group consisting of O, N and S in any combination. Any heteroaryl substituent is attached by a single bond, and is optionally and independently substituted one or more times with H, halogen, alkyl having 1-6 carbons, or alkoxy having 1-6 carbons. Selected examples of heteroaryl substituents are pyrrole, thiophene, or furan (single ring, single hetero atom), oxazole, isoxazole, oxadiazole, or imidazole (single ring, multiple hetero atoms). Examples of multi-ring heteroaryl groups include benzoxazole, benzothiazole, benzimidazole (multi-ring, multiple hetero atoms), benzofuran or indole (multi-ring, single hetero atom).

As used herein, "a pharmaceutically acceptable salt," "a biologically compatible salt" or a "biologically compatible counterion" is a counterion that is not toxic as used, and does not have a substantially deleterious effect on biomolecules. Examples of such salts or counterions include, among others, $K^+$, $Na^+$, $Cs^+$, $Li^+$, $Ca^{++}$, $Mg^{++}$, $Cl^-$, $Br^-$, $I^-$, $AcO^-$, sulfate, alkane sulfonate, arylsulfonate, phosphate, perchlorate, tetrafluoroborate, tetraaryloboride, nitrate, alkylammonium or alkoxyammonium salts, and anions of aromatic oar aliphatic carboxylic acids. Preferred counterions are chloride, iodide, perchlorate and various sulfonates.

As used herein, "alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

As used herein, "alkenyl" refers to alkenyl groups having from 2 to 22 carbon atoms, preferably 2 to 4 carbon atoms, and having at least 1 and preferably from 1 to 2 sites of alkenyl unsaturation. Such groups are exemplified, for example, by vinyl, allyl, and but-3-en-1-yl.

As used herein, "alkenoxy" refers to the group —O-alkenyl wherein alkenyl is defined herein. Alkenoxy includes, by way of example, vinyloxy, allyloxy, 1-butenoxy, 2-butenoxy, 2-pentenoxy, 3-pentenoxy, 4-pentenoxy.

As used herein, "heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings may be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

As used herein, "OMEGA" refers to a saturated or unsaturated, substituted or unsubstituted, cyclic substituent that has a total of 2-16 ring carbon atoms in 1-2 alicyclic, heteroalicyclic, aromatic, or heteroaromatic rings containing 1-4 heteroatoms (wherein the heteroatoms are O, N, or S) that is directly bonded to the pyridinium or quinolinium ring systems by a single bond. OMEGAs that are alicyclic ring systems may be either linked or fused. Examples of OMEGA are substituted or unsubstituted cyclohexyls, cyclohexenyls, morpholinyls, and piperidinyls. Examples of OMEGA that are aromatic include substituted or unsubstituted naphthyls, phenyls, thienyls, benzothiazolyls, furanyls, oxazolyls, benzoxazolyls, and pyridinyls. Substituents on OMEGA are independently hydrogen, halogen, alkyl, perfluoroalkyl, amino, alkylamino, dialklyamino, alkoxy or carboxyalkyl, each alkyl having 1-6 carbons. Preferred embodiments of OMEGA are substituted or unsubstituted naphthyl, phenyl, thienyl, morpholinyl, and cyclohexyl, more preferably, substituted or unsubstituted phenyl.

As used herein, "sulfo" refers to sulfonic acid or sulfonate.

As used herein, "halogen" refers to fluorine, chlorine, bromine, or iodine.

As used herein, "ROS probes," "ROS dyes," and "ROS sensors" refer interchangeably to novel reduced dye compounds disclosed herein, which compounds are probes for detecting reactive oxygen species (ROS) and measuring oxidative stress in cells in vitro or in vivo.

As used herein, the term "dye" refers to a compound that emits light to produce an observable detectable signal.

The reduced dye compounds disclosed herein may exist in unsolvated forms as well as solvated forms, including hydrated forms. These reduced dye compounds may exist in multiple crystalline or amorphous forms. In general, all physical forms are equivalent for the uses described herein and are intended to be within the scope of the present invention. The reduced dye compounds disclosed herein may possess asymmetric carbon atoms (i.e., chiral centers) or double bonds; the racemates, diastereomers, geometric isomers and individual isomers of the reduced dye compounds described herein are within the scope of the present invention. The reduced dye compounds described herein may be prepared as a single isomer or as a mixture of isomers.

Where substituent groups specified by their conventional chemical formulae, written from left to right, they equally encompass the chemically identical substituents, which would result from writing the structure from right to left, e.g., —$CH_2O$— is intended to also recite —$OCH_2$—.

It will be understood that the chemical structures that are used to define reduced dye compounds of the present invention are each representations of one of the possible resonance structures by which each given structure can be represented. Further, it will be understood that by definition, resonance structures are merely a graphical representation used by those of skill in the art to represent electron delocalization, and that the present invention is not limited in any way by showing one particular resonance structure for any given structure.

Where a disclosed reduced dye compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound. For example,

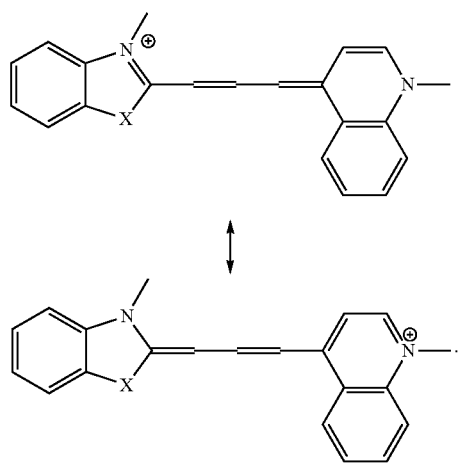

Reduced Dye Compounds and Compositions:

In certain embodiments, novel reduced dye compounds (i.e., ROS probes) having structural formula (I) are provided:

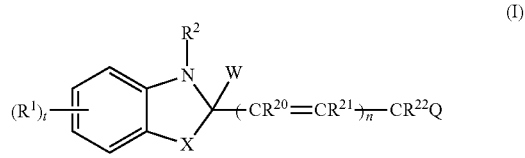

wherein
each $R^1$, which may be the same or different, is independently H; $C_1$-$C_6$ alkyl; trifluoromethyl; halogen; —$OR^8$, —$SR^8$, or —($NR^8R^9$), where $R^8$ and $R^9$, which may be the same or different, are independently H; $C_1$-$C_6$ alkyl; or 1-2 alicyclic hetroalicyclic, aromatic or heteroaromatic rings having a total of 3-16 ring atoms, wherein the heteroatoms are O, N, or S; or $R^8$ and $R^9$ taken in combination are —$(CH_2)_2$-L-$(CH_2)_2$— where L is a single bond; —$CH_2$—; —O—; or —$NR^{10}$, where $R^{10}$ is H or a $C_1$-$C_6$ alkyl;

t is 1, 2, 3 or 4;

$R^2$ is a substituted or unsubstituted $C_1$-$C_6$ alkyl;

X is O; S; Se; $NR^{15}$, where $R^{15}$ is H or a $C_1$-$C_6$ alkyl; or $CR^{16}R^{17}$, where $R^{16}$ and $R^{17}$, which may be the same or different, are independently H or $C_1$-$C_6$ alkyl, or the carbons of $R^{16}$ and $R^{17}$ taken in combination complete a five- or six-membered saturated ring;

Q has the formula Q1 or Q2:

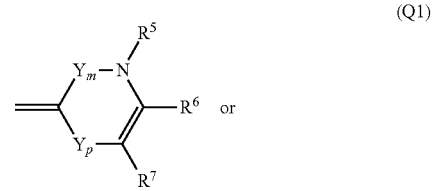

wherein
Y is —$CR^3$=$CR^4$—;

p and m are 0 or 1, such that p+m=1;

$R^5$ is a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; or an OMEGA;

$R^3$, $R^4$, $R^6$ and $R^7$, which may be the same or different, are each independently H; halogen; a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; —$OR^8$; —$SR^8$; —($NR^8R^9$), as defined previously; —$OSO_2R^{19}$, where $R^{19}$ is a $C_1$-$C_6$ alkyl, $C_1$-$C_6$ perfluoroalkyl, or aryl; or an OMEGA; or $R^6$ and $R^7$, taken in combination are —$(CH_2)_v$—, where v is 3 or 4, or $R^6$ and $R^7$ form a fused aromatic ring according to the formula Q2; $R^{11}$, $R^{12}$, $R^{13}$ and $R^{14}$, which may be the same or different, are each independently H; a $C_1$-$C_6$ alkyl, $C_1$-$C_6$ alkenyl, $C_1$-$C_6$ polyalkenyl, $C_1$-$C_6$ alkynyl or $C_1$-$C_6$ polyalkynyl group; a halogen; an OMEGA; or —OH, —$OR^8$; —$SR^8$; —($NR^8R^9$), as defined previously;

OMEGA is a saturated or unsaturated, substituted or unsubstituted, cyclic substituent that has a total of 2-16 ring carbon atoms in 1-2 alicyclic, heteroalicyclic, aromatic, or heteroaromatic rings, containing 1-4 heteroatoms wherein the heteroatoms are O, N, or S, that is unsubstituted or optionally substituted one or more times, independently, by halogen, alkyl, perfluoroalkyl, amino, alkylamino, dialkylamino, alkoxy or carboxyalkyl, having 1-6 carbons, and that is attached as $R^3$, $R^4$, $R^5$, $R^{11}$, $R^{12}$, $R^{13}$, or $R^{14}$ by a single bond, and, where more than one of $R^3$, $R^4$, $R^5$, $R^{11}$, $R^{12}$, $R^{13}$, and $R^{14}$ is an OMEGA, each OMEGA is optionally the same or different;

$R^{20}$, $R^{21}$ and $R^{22}$ are independently H, $C_1$-$C_6$ alkyl, $C_3$-$C_{10}$ cycloalkyl, aryl or heteroaryl;

W is H or D in either the R or S configuration; and n is 0, 1, 2, or 3.

In certain embodiments, novel reduced dye compounds (i.e., ROS probes) having structural formula (II) are provided:

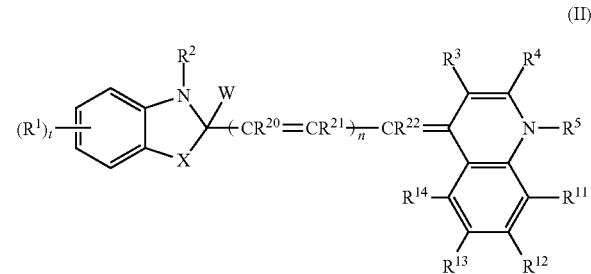

(II)

wherein each $R^1$, which may be the same or different, is independently H; $C_1$-$C_6$ alkyl; trifluoromethyl; halogen; —$OR^8$, —$SR^8$, or —($NR^8R^9$), where $R^8$ and $R^9$, which may be the same or different, are independently H; $C_1$-$C_6$ alkyl; or 1-2 alicyclic hetroalicyclic, aromatic or heteroaromatic rings having a total of 3-16 ring atoms, wherein the heteroatoms are O, N, or S; or $R^8$ and $R^9$ taken in combination are —($CH_2$)$_2$-L-($CH_2$)$_2$— where L is a single bond; —$CH_2$—; —O—; or —$NR^{10}$, where $R^{10}$ is H or a $C_1$-$C_6$ alkyl;

t is 1, 2, 3 or 4;

$R^2$ is a substituted or unsubstituted $C_1$-$C_6$ alkyl;

$R^5$ is an alkyl, alkenyl, polyalkenyl, alkynyl or polyalkynyl group having 1-6 carbons; or an OMEGA;

$R^3$, $R^4$, $R^{11}$, $R^{12}$, $R^{13}$ and $R^{14}$ are each independently H; halogen; an alkyl, alkenyl, polyalkenyl, alkynyl or polyalkynyl group having 1-6 carbons; —$OR^8$; —$SR^8$; —($NR^8R^9$), as defined previously; —$OSO_2R^{19}$, where $R^{19}$ is a $C_1$-$C_6$ alkyl, $C_1$-$C_6$ perfluoroalkyl, or aryl; or an OMEGA;

OMEGA is a saturated or unsaturated, substituted or unsubstituted, cyclic substituent that has a total of 2-16 ring carbon atoms in 1-2 alicyclic, heteroalicyclic, aromatic, or heteroaromatic rings, containing 1-4 heteroatoms wherein the heteroatoms are O, N, or S, that is unsubstituted or optionally substituted one or more times, independently, by halogen, alkyl, perfluoroalkyl, amino, alkylamino, dialkylamino, alkoxy or carboxyalkyl, having 1-6 carbons, and that is attached as $R^3$, $R^4$, $R^5$, $R^{11}$, $R^{12}$, $R^{13}$, or $R^{14}$ by a single bond, and, where more than one of $R^3$, $R^4$, $R^5$, $R^{11}$, $R^{12}$, $R^{13}$, and $R^{14}$ is an OMEGA, each OMEGA is optionally the same or different;

X is O; S; Se; $NR^{15}$, where $R^{15}$ is H or a $C_1$-$C_6$ alkyl; or $CR^{16}R^{17}$, where $R^{16}$ and $R^{17}$, which may be the same or different, are independently H or $C_1$-$C_6$ alkyl, or the carbons of $R^{16}$ and $R^{17}$ taken in combination complete a five- or six-membered saturated ring;

$R^{20}$, $R^{21}$, and $R^{22}$ are independently H, $C_1$-$C_6$ alkyl, $C_3$-$C_{10}$ cycloalkyl, aryl or heteroaryl;

W is H or D in either the R or S configuration; and n is 0, 1, 2, or 3.

In certain embodiments, the reduced dye compounds provided herein comprise an OMEGA that is selected from substituted or unsubstituted naphthyl, phenyl, thienyl, morpholino and cyclohexyl, more preferably substituted or unsubstituted phenyl. In an illustrative embodiment, $R^5$ is an OMEGA.

In other embodiments, although $R^1$ on the benzazolium ring system is usually H, incorporation of a non-hydrogen substituent $R^1$ may be used to fine tune the absorption and emission spectrum of the resulting dye. In yet further embodiments, the reduced dye compounds disclosed herein contain no more than one $R^1$ substituent that is non-hydrogen.

In yet other embodiments of the reduced dye compounds provided herein, the substituent $R^2$ may be a $C_1$-$C_6$ alkyl, preferably methyl or ethyl, more preferably methyl. In other embodiments, the substituent $R^2$ may be a substituted $C_1$-$C_6$ alkyl, preferably substituted with one or more aryl, ammonium or trialkylammonium groups.

The methine bridge consists of 1, 3 or 5 methine (—CR=) groups that bridge the benzazolium portion of the molecule and the pyridinium portion in such a way as to permit extensive electronic delocalization. When n=0, the dyes are unsymmetrical monomethine dyes that generally stain with a green fluorescence; when n=1, the dyes are trimethine dyes that generally stain with a red fluorescence; when n=2, the dyes are pentamethine dyes that generally stain with a non-visible, near infrared fluorescence. Additional non-hydrogen substitutents on the heterocyclic ring systems may further affect the spectral properties of the dyes.

The methine substituents $R^{20}$, $R^{21}$ and $R^{22}$ are independently H, $C_1$-$C_6$ alkyl, $C_3$-$C_{10}$ cycloalkyl, aryl or heteroaryl, where n=1 or 2, each $R^{21}$ and $R^{22}$ varies independently. In certain embodiments, only the substituent on the central carbon of the methine bridge is nonhydrogen ($R^{20}$ where n=0, $R^{21}$ where n=1, and the centrally located $R^{22}$ where n=2). In certain embodiments, where a methine substituent is nonhydrogen, it is an alkyl. In certain embodiments, where a methine substituent is nonhydrogen, it is an aryl. Typically, $R^{20}$, $R^{21}$ and $R^{22}$ are hydrogen. Where $R^{20}$, $R^{21}$ and $R^{22}$ are nonhydrogen, preferably n=1.

In certain embodiments, the pyridinium or quinolinium ring system contains a ring fragment Y that is —$CR^3$=$CR^4$—, with subscripts p and m equal to 0 or 1, such that p+m=1. In certain embodiments, the ring contains a 6-membered pyridinium-based heterocycle according to structure (V) or (VI):

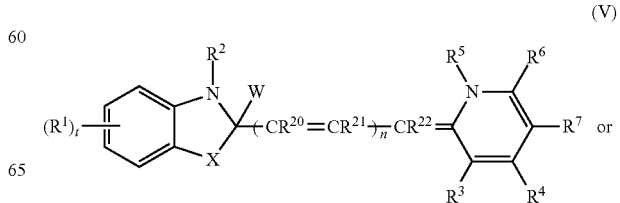

(V)

or

-continued

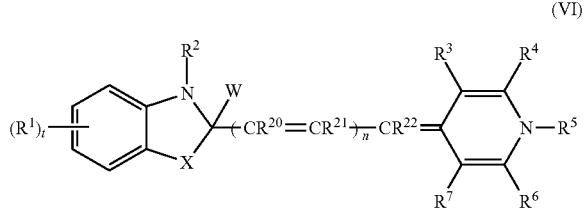

(VI)

wherein $R^1$, $R^2$, $R^3$, $R^4$, $R^5$, $R^6$, $R^{20}$, $R^{21}$, $R^{22}$, X, W, n and t are as defined previously herein. In preferred embodiments, m=1 and p=0 (4-pyridinium, structure (VI)).

In certain embodiments, the substituents on the second heterocyclic ring system, $R^3$, $R^4$, $R^6$ and $R^7$ are each independently H, halogen, alkyl, or —$OR^8$, —$SR^8$, —($NR^8R^9$), where $R^8$ and $R^9$ are methyl or ethyl; or an OMEGA; or $R^6$ and $R^7$ taken in combination form a fused 6-membered aromatic ring. In certain embodiments, $R^4$ may be a $C_1$-$C_6$ alkyl. In yet other embodiments where $R^6$ and $R^7$ taken in combination form a fused 6-membered aromatic ring, the quinolinium derivatives contain a fused aromatic ring according to the structure (VII):

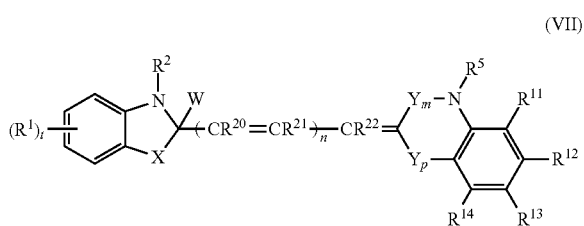

(VII)

wherein $R^1$, $R^2$, $R^5$, $R^{11}$, $R^{12}$, $R^{13}$, $R^{14}$, $R^{20}$, $R^{21}$, $R^{22}$, W, X, Y, m, n, p, and t are as defined previously herein.

In certain illustrative embodiments, the reduced cyanine dye compound is a quinolinium wherein m=1 and p=0 (4-quinolinium, structure (VI)). In certain embodiments, the ring substituents are each independently H; halogen; alkyl; or —$OR^8$, —$SR^8$, —($NR^8R^9$), where $R^8$ and $R^9$ are methyl or ethyl; or an OMEGA.

In certain embodiments, the reduced dye compounds contain exactly two non-hydrogen substitutents on the second heterocyclic ring, one of which is an OMEGA. In certain preferred embodiments, $R^5$ is an OMEGA. In certain embodiments, $R^5$ is an OMEGA and the substituent adjacent to $R^5$ ($R^6$ for pyridiniums, $R^4$ for quinoliniums, and $R^{11}$ for 2-quinoliniums) is a non-hydrogen substituent. In certain embodiments, the substituent adjacent to $R^5$ is halogen; —$OR^8$, —$SR^8$, —($NR^8R^9$) or —$OSO_2R^{19}$; more preferably halogen. In certain embodiments, $R^5$ is —$OR^8$, —$SR^8$, or —($NR^8R^9$), preferably —($NR^8R^9$). In certain embodiments, the substituent adjacent $R^5$ is an OMEGA. In certain embodiments, $R^5$ is phenyl. $R^8$ and $R^9$ are as defined previously.

In certain embodiments of the reduced dye compounds, $R^2$ is methyl or ethyl, $R^4$ is a $C_1$-$C_6$ alkyl, $R^5$ is phenyl, X is S, and n is 0.

The reduced nucleic acid binding cyanine dyes disclosed herein, which are generally membrane permeable and may therefore accumulate in cells, are unable to bind nucleic acid and exhibit little or no fluorescence compared to the corresponding oxidized dyes. Upon intracellular reaction with, i.e., detection of, ROS, the reduced dyes disclosed herein are oxidized thereby affording a high-affinity nucleic acid binding cyanine dye, which stains nucleic acids with substantial fluorescence intensity upon exposure to light of sufficient wavelength. The reduced dyes disclosed herein, in combination with, for example, probes for mitochondrial membrane potential, plasma membrane permeability, and/or caspase activation, may be used to differentiate hepatotoxic compounds from non-toxic compounds.

The reduced dye compounds disclosed herein display enhanced stability to auto-oxidation, have tunable emission wavelengths, and nanomolar to millimolar sensitivity for ROS. Unexpectedly, unlike other prior art ROS probes, the reduced dye compounds disclosed herein also display resistance to formaldehyde fixation and detergent permeabilization. In addition, the reduced dye compounds disclosed herein may be used under more physiological conditions, such as in complete media; unlike other prior art ROS probes. Furthermore, there is no requirement for a post-staining washing step when using the reduced dye compounds disclosed herein, whereas other prior art ROS probes have such a requirement.

In certain embodiments, the first and second heterocyclic ring systems of the reduced dye compounds disclosed herein are optionally further substituted with a variety of substituents or are fused to additional rings that are optionally further substituted, which substitution fine tunes the absorption and emission spectrum of the resulting reduced cyanine compound and, indirectly, that of the corresponding oxidized (e.g., by ROS) dye compound as well.

In certain embodiments reduced dye compounds having structural formula (VIII) are provided:

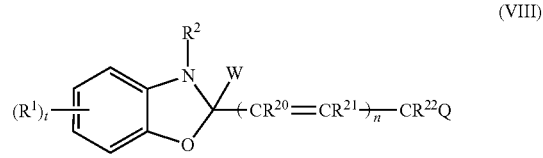

(VIII)

wherein

Q, W, $R^1$, $R^2$, $R^{20}$, $R^{21}$, $R^{22}$, n, and t are as described previously herein.

In certain embodiments reduced dye compounds having structural formula (IX) are provided:

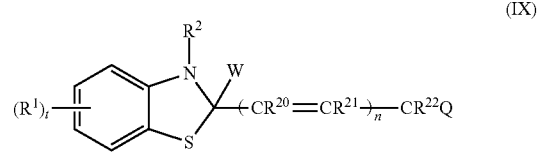

(IX)

wherein

Q, W, $R^1$, $R^2$, $R^{20}$, $R^{21}$, $R^{22}$, n, and t are as described previously herein.

In certain embodiments reduced dye compounds having structural formula (X) are provided:

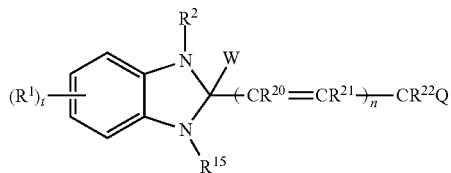

wherein

Q, W, $R^1$, $R^2$, $R^{15}$, $R^{20}$, $R^{21}$, $R^{22}$, n, and t are as described previously herein.

In certain embodiments reduced dye compounds having structural formula (XI) are provided:

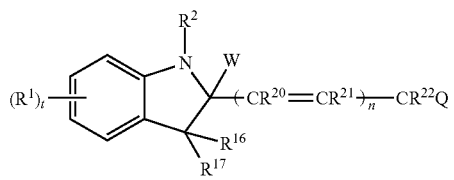

wherein

Q, W, $R^1$, $R^2$, $R^{16}$, $R^{17}$, $R^{20}$, $R^{21}$, $R^{22}$, n, and t are as described previously herein.

The choice of X moieties in structural formulae (I), (II), (III) and (IV), as well as the length of the polymethine bridge between the heterocyclic ring systems, have an effect on the absorption and fluorescence emission properties of the reduced dye compounds disclosed herein. The spectral properties of the resulting reduced dye compounds may be tuned accordingly by careful selection of X. In certain illustrative embodiments, X is S.

The reduced dye compounds disclosed herein are either hydrocyanine or deuterocyanine, with both types being suitable for the compositions, methods of use, and kits described herein. These reduced dyes display enhanced stability to auto-oxidation, have tunable emission wavelengths, and nanomolar to millimolar sensitivity for ROS. Furthermore, oxidation of a given deuterocyanine generates the identical cyanine as its hydrocyanine analogue, thereby permitting these probes to be used interchangeably with existing protocols for ROS sensors. Although the hydrocyanine dyes disclosed herein exhibit improved stability to auto-oxidation in aqueous solution, compared to prior art ROS probes such as DHE, their background oxidation in cell culture exceeds that of the corresponding deuterocyanine dyes, which dyes may display greater stability to auto-oxidation and thereby exhibit lower levels of background fluorescence. Without wishing to be bound by theory, deuterium substitution in the hydrocyanine molecules at the appropriate position may render the molecule more stable to spontaneous oxidation (to air, upon storage, etc.), while still allowing for adequate reactivity in the actual ROS sensing event where the reaction rate difference between H and D would be miniscule relative to the background oxidation event rate.

In certain embodiments, compositions are provided for the detection of reactive oxygen species (ROS), the compositions comprising:

a) one or more of the reduced dye compounds described herein; and b) a carrier, wherein the reduced dye compounds are present in an amount effective to detect the presence of ROS upon reaction with the ROS.

The reduced dye compounds disclosed herein are typically solids at room temperature. Therefore, the compounds will generally be dissolved or suspended in a carrier for use or administration as a composition. The exact concentration of reduced dye to be used is dependent upon the experimental conditions and the desired results, and optimization of experimental conditions is typically required to determine the best concentration of reduced dye to be used in a given application. The concentration of reduced dye typically ranges from nanomolar to millimolar, preferably from nanomolar to micromolar. The concentrations of the reduced dye compounds are readily determined from methods known in the art for use of similar compounds under comparable conditions for the desired optical response.

In certain embodiments, compositions are provided for the detection of ROS, the compositions comprising:

a) one or more of the reduced dye compounds described herein; and b) a carrier, wherein the reduced dye compounds are present in an amount effective to detect the presence of ROS upon reaction with the ROS, and wherein the composition is suitable for in vivo use.

Typically for in vivo use, the concentration of the reduced dye is the minimum amount required to yield a detectable signal in the sample within a reasonable time, with minimal background fluorescence. The exact concentration of reduced dye to be used is dependent upon the experimental conditions and the desired results. In certain embodiments, the amount of dye is from about 50 µg/kg to about 50 g/kg, preferably from about 50 µg/kg to about 10 g/kg, more preferably from about 50 µg/kg to about 1 g/kg, most preferably from about 50 µg/kg to about 0.1 g/kg.

For in vivo use, the reduced dye compounds provided herein will typically be combined with one or more carriers. As used herein, the "carrier" refers to all components present in the composition other than the reduced dyes. The term "carrier" includes, but is not limited to, solvents, suspending agents, dispersants, buffers, pH modifying agents, isotonicity modifying agents, preservatives, antimicrobial agents, additives, excipients, and combinations thereof. Additives include those that are useful for processing or preparing the composition, those that may aid in the incorporation or stability of the compositions, or those that may be useful in modifying performance of the composition. Excipients include any number of other medically or pharmaceutically acceptable agents such as preservatives, lipids, fatty acids, waxes, surfactants, plasticizers, porosigens, antioxidants, bulking agents, buffering agents, chelating agents, cosolvents, water-soluble agents, insoluble agents, metal cations, anions, salts, osmotic agents, synthetic polymers, biological polymers, hydrophilic polymers, polysaccharides, sugars, hydrophobic polymers, hydrophilic polymers, and combinations thereof.

For in vivo applications, the formulations may be administered by a variety of routes. Typically, the compounds are formulated for parenteral administration including, but not limited to, intravenous, intraarterial, intramuscular, intraperitoneal, subcutaneous, intradermal, infusion, subconjunctive and intracatheter (e.g., aurologic delivery), as well as administration via external scopic techniques such as, for example, arthroscopic or endoscopic techniques.

The compositions disclosed herein may be administered to specific locations (e.g., local delivery) including, but not limited to, intrathecal, intracardiac, intraosseous (e.g., bone marrow), stereotactic-guided delivery, infusion delivery, CNS delivery, stereo-tactically administered delivery, orthopaedic delivery (e.g., delivery to joints or into bone), cardiovascular delivery, inter-, intra- and para-ocular delivery (including intravitreal and sclera, retrobulbar and sub-tenous delivery), as well as delivery to any multitude of other sites, locations, organs, etc.

In certain embodiments, compositions are provided for the detection of ROS, the compositions comprising:
a) one or more of the reduced dye compounds described herein; and
b) a carrier,
wherein the reduced dye compounds are present in an amount effective to detect the presence of ROS upon reaction with the ROS, and wherein the composition is suitable for in vitro use.

Typically for in vitro use, the concentration of the reduced dye compounds contacted with cells is from about 1 µM to about 100 µM. However, the specific concentration may be readily adjusted based on the assay being performed. In general, the reduced dye compounds disclosed herein will be dissolved or suspended in an appropriate solvent suitable for the intended application. Suitable solvents include, but are not limited to, aqueous solvents, such as water, PBS, saline, organic solvents, such as DMSO and alcohols, and combinations thereof. The reduced dye compounds disclosed herein may also or alternatively be encapsulated in various nanostructures to improve cell delivery. Suitable nanostructures include, but are not limited to, liposomes, microparticles, such as polymeric microparticles, and micelles, such as polymeric micelles formed from block copolymers.

Methods of Use:

In certain embodiments methods are provided for the detection of reactive oxygen species (ROS) in a sample, the method comprising the steps of:
a) contacting the sample with an effective amount of one or more of the reduced dye compounds provided herein or the compositions provided herein; and
b) determining if the reduced dye compound has been oxidized.

In certain embodiments, methods are provided for the detection of ROS in a sample, the method comprising:
a) contacting the sample with an effective amount of one or more of the reduced dye compounds provided herein;
b) measuring the fluorescence intensity of the one or more dye compounds; and
c) determining if the reduced dye compound has been oxidized;
wherein an increase in fluorescence intensity is indicative of the presence of ROS in the sample.

In certain embodiments, methods are provided for the detection of ROS in a sample, the method comprising:
a) contacting the sample with an effective amount of one or more of the compositions comprising one or more of the reduced dye compounds provided herein;
b) measuring the fluorescence intensity of the one or more compositions; and
c) determining if the reduced dye compound has been oxidized;
wherein an increase in fluorescence intensity is indicative of the presence of ROS in the sample.

In certain embodiments, the reduced dye compounds disclosed herein may be used as diagnostic tools to evaluate or detect a variety of diseases and disorders or markers for diseases or disorders, characterized by the production or overproduction of ROS in vivo or to detect or quantify ROS in a sample in vitro. The fluorescence emitted by the oxidized dyes, which dyes are produced upon reaction of the reduced dyes disclosed herein with ROS, may be measured using fluorescence spectroscopy or fluorescence microscopy depending on the application. Exemplary methods of fluorescence microscopy include, but are not limited to, confocal laser scanning microscopy, total internal reflection fluorescence microscopy, histological analysis via fluorescence, flow cytometry, analyses using plate readers, such as fluorescence microplate readers, standard or mini fluorometers, or epifluorescence microscopes.

In certain embodiments, the reduced dye compounds disclosed herein, and compositions comprising those dyes, may be used as diagnostic tools in vivo to evaluate or detect a variety of diseases and disorders characterized by the production or overproduction of ROS. Exemplary diseases and disorders include, but are not limited to, carotid artery injuries, atherosclerosis, hypertension, cancers, diseases and disorders characterized by inflammation, radiation-induced late normal tissue damage, tissue damage due to chemotherapy, reperfusion after ischemia, or transplantation, diabetes, such as type I diabetes (T1D), neurodegenerative diseases, such as Alzheimer's disease, Parkinson's disease, amyotrophic lateral sclerosis (ALS) and Huntington's disease, cerebrovascular disease, cystic fibrosis, chronic kidney disease, cardiovascular disease, preeclampsia and ophthalamic diseases (i.e., diseases of the eye). In addition, the reduced dye compounds disclosed herein may be used in positron emission tomography (PET) as contrast agents, imaging of biomolecules, and photoacoustic imaging.

In certain embodiments, the reduced dye compounds disclosed herein, and compositions comprising those dyes, may be used for a variety of in vitro or ex vivo assays. For example, the reduced dyes may be used for single cell imaging or to assay a cell suspension, during which the dye(s) are loaded into cells by incubation with the cells for a sufficient period of time. Specific assays include, but are not limited to, those with live organ cultures as well as cell culture assays.

The general procedure for using the reduced dyes disclosed herein is as follows. One or more of the reduced dye compounds, or compositions comprising one or more of the reduced dye compounds, disclosed herein is administered in vivo or in vitro to contact a biological sample, i.e., cells, cell cultures, tissues, organs, serum, bodily fluids, biological fluids, etc. The one or more reduced dye disclosed herein may be formulated with one or more carriers depending on the assay. The one or more reduced dye compound is incubated with the sample for a period of time sufficient for the one or more reduced dye to react with reactive oxygen species (ROS) present in the sample. After such time, the sample is analyzed for fluorescence intensity. The fluorescence intensity after incubation is compared to the fluorescence intensity of the one or more reduced dye. An increase in the fluorescence intensity of the dye in the biological sample indicates oxidation of the dye, and thus the presence of reactive oxygen species (ROS). The increased fluorescence may be measured or detected using the techniques listed above.

Kits:

In certain embodiments kits are provided for detecting reactive oxygen species (ROS) in a sample, the kits comprising:
a) one or more of the reduced dye compounds provided herein; and
b) one or more containers.

In certain embodiments, kits are provided for detecting reactive oxygen species (ROS) in a sample, the kits comprising:
a) one or more of the compositions comprising reduced dye compounds provided herein; and
b) one or more containers.

In certain embodiments, kits are provided for detecting reactive oxygen species (ROS) in a sample, the kit comprising:
a) one or more of the unreduced cyanine dye compounds provided herein;
b) one or more reducing agents; and
c) one or more containers.

In certain embodiments, the kits provided herein further comprise instructions for performing an assay for detecting one or more reactive oxygen species (ROS) in a sample. In certain embodiments, the kits provided herein are suitable for use with in vivo assays. In certain embodiments, the kits provided herein are suitable for use with in vitro assays. Non-limiting examples of reducing agents that may be used include, but are not limited to, metal salts, such as $LiAlH_4$, $NaBH_4$, $Zn(BH_4)_2$, compounds containing a $Sn^{2+}$ ion, sulfite compounds, diisobutyl aluminum hydride (DIBAH), oxalic acid, formic acid, ascorbic acid, phosphites, hypophosphate, hypophorphorous acid, dithiothreitol (DTT), and compounds containing the $Fe^{2+}$ ion. Any of these may have the hydrogen replaced by deuterium, for example, $NaBD_4$, $Zn(BD_4)_2$, $LiAlD_4$. In certain embodiments, the reducing agent may be $NaBH_4$ or $NaBD_4$.

As used herein, the term "kit" refers to a packaged set of related components, typically one or more reduced dye compounds or compositions comprising the reduced dye compounds. In certain embodiments, the kits provided herein comprise one or more of the reduced dye compounds or compositions described herein, one or more carriers suitable for in vitro or in vivo applications, and one or more containers in which to store the one or more reduced dyes and/or one or more carriers, such as solvents, buffers, stabilizers, pH adjusting agents, etc. In certain embodiments, the kits provided herein comprise one or more of the unreacted cyanine dye compounds having structural formulae (III) or (IV), one or more reducing agents, one or more carriers suitable for in vitro or in vivo applications, and one or more containers in which to store the one or more reduced dyes and/or one or more carriers, such as solvents, buffers, stabilizers, pH adjusting agents, etc. In certain embodiments, the kits provided herein optionally contains instructions for how to prepare the one or more reduced dyes or how to prepare a composition containing the one or more reduced dye, how to administer the dye or composition containing the dye, and how to detect oxidation of the dye (e.g., excitation wavelength and emission wavelength). In a preferred embodiment, the kit contains instructions for performing an assay that detects the presence of one or more reactive oxygen species (ROS). In certain embodiments, the kits provided herein may further contain one or more pieces of equipment to administer the dye, or composition containing the dye, including, but not limited to, syringes, pipettes, pipette bulbs, spatulas, vials, syringe needles, and various combinations thereof.

Methods of Preparation/Synthesis:

The reduced dyes disclosed herein suitable for the compositions, methods of use, and kits described herein are generally prepared by reduction of the corresponding cyanine dye with a reducing agent. For example, hydrocyanine and deuterocyanine dyes disclosed herein may be synthesized from their corresponding cyanine dyes via a one-step reduction using a reducing agent such as sodium borohydrate ($NaBH_4$) or sodium borodeuteride ($NaBD_4$). The reduced dyes disclosed herein exhibit little or no fluorescence (due to the disrupted π-conjugation) compared to their corresponding cyanine dyes. However, upon reaction with ROS, the reduced dyes are oxidized (regenerating a high-affinity nucleic acid binding cyanine dye having extended π-conjugation) thereby affording a substantial increase in fluorescence intensity when exposed to light of sufficient wavelength.

In certain embodiments, processes are provided for preparing reduced dye compounds (i.e., ROS probes) having structural formula (I):

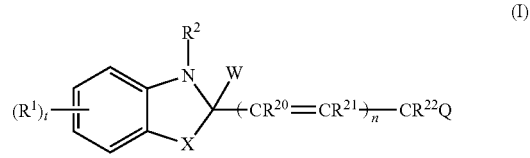

the process comprising:

a) reacting a cyanine compound having structural formula (III):

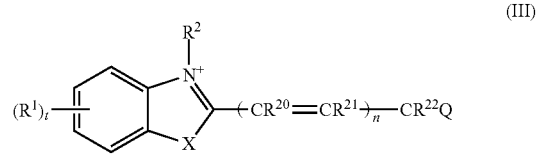

with a reducing agent, wherein:

Q, W, X, $R^1$, $R^2$, $R^{20}$, $R^{21}$, $R^{22}$, n, and t are as defined previously herein. Non-limiting examples of reducing agents that may be used include, but are not limited to, metal salts, such as $LiAlH_4$, $NaBH_4$, $Zn(BH_4)_2$, compounds containing a $Sn^{2+}$ ion, sulfite compounds, diisobutyl aluminum hydride (DIBAH), oxalic acid, formic acid, ascorbic acid, phosphites, hypophosphate, hypophorphorous acid, dithiothreitol (DTT), and compounds containing the $Fe^{2+}$ ion. Any of these may have the hydrogen replaced by deuterium, for example, $NaBD_4$, $Zn(BD_4)_2$, $LiAlD_4$. In certain embodiments, the reducing agent may be $NaBH_4$ or $NaBD_4$.

In certain embodiments, processes are provided for preparing reduced dye compounds (i.e., ROS probes) having structural formula (II):

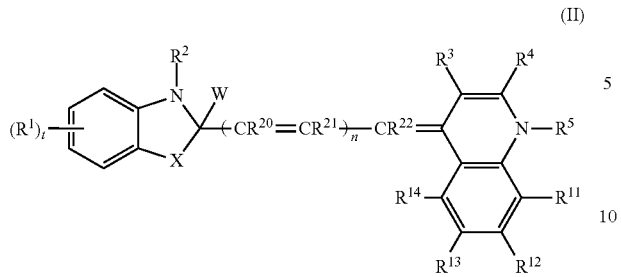

(II)

the process comprising:

a) reacting a cyanine compound having structural formula (IV):

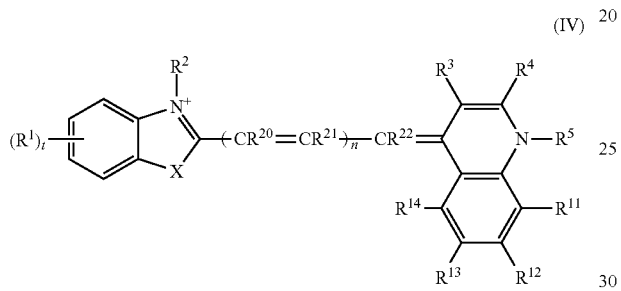

(IV)

with a reducing agent, wherein:

W, X, $R^1$, $R^2$, $R^3$, $R^4$, $R^5$, $R^{11}$, $R^{12}$, $R^{13}$, $R^{14}$, $R^{20}$, $R^{21}$, $R^{22}$, n, and t are as defined previously herein. Non-limiting examples of reducing agents that may be used include, but are not limited to, metal salts, such as $LiAlH_4$, $NaBH_4$, $Zn(BH_4)_2$, compounds containing a $Sn^{2+}$ ion, sulfite compounds, diisobutyl aluminum hydride (DIBAH), oxalic acid, formic acid, ascorbic acid, phosphites, hypophosphate, hypophorphorous acid, dithiothreitol (DTT), and compounds containing the $Fe^{2+}$ ion. Any of these may have the hydrogen replaced by deuterium, for example, $NaBD_4$, $Zn(BD_4)_2$, $LiAlD_4$. In certain embodiments, the reducing agent may be $NaBH_4$ or $NaBD_4$.

In one illustrative embodiment of such a process, a compound of structural formula (II) is prepared as shown in General Scheme shown below:

General Scheme

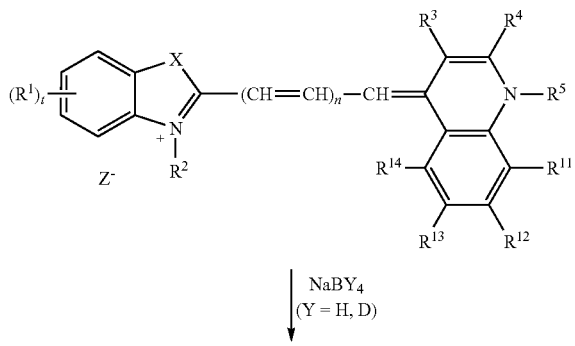

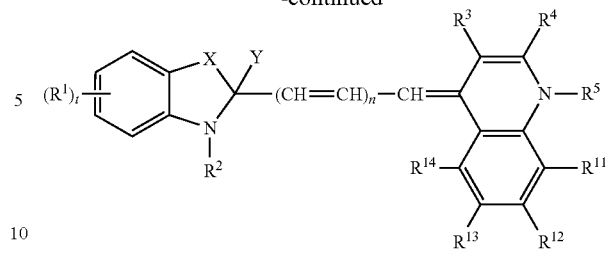

wherein $Z^-$ is a biologically compatible counterion; and

X, $R^1$, $R^2$, $R^3$, $R^4$, $R^5$, $R^{11}$, $R^{12}$, $R^{13}$, $R^{14}$, n, and t are a defined previously herein.

In another illustrative embodiment of such a process, a compound of structural formula (I) is prepared as shown in Scheme I:

Scheme I

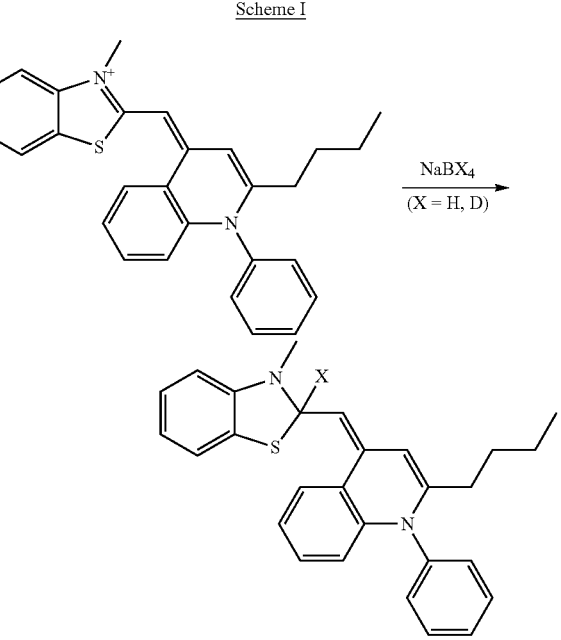

1, X = H
2, X = D

In another illustrative embodiment of such a process, a compound of structural formula (I) is prepared as shown in Scheme II (see below):

Scheme II

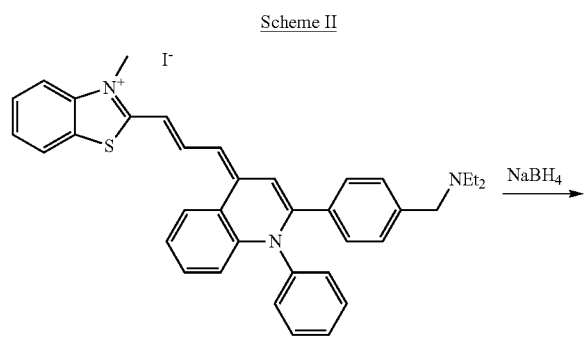

-continued

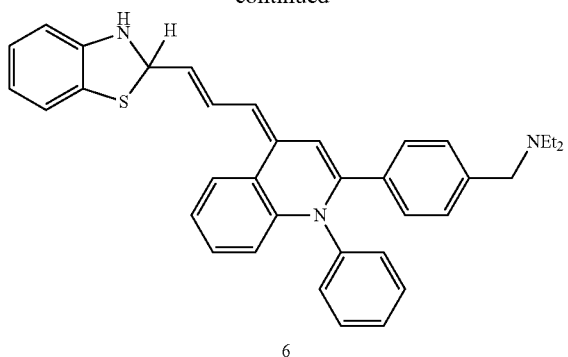

6

A detailed description of the present invention having been provided above, the following examples are given for the purpose of illustrating the invention and shall not be construed as being a limitation on the scope of the invention or claims.

EXAMPLES

I. Chemical Synthesis of Reduced Dye Compounds (ROS Probes) Disclosed Herein

Example 1

Synthesis of (Z)-2-((2-butyl-1-phenylquinolin-4(1H)-ylidene)methyl)-3-methyl-2,3-dihydrobenzo[d]thiazole (1)

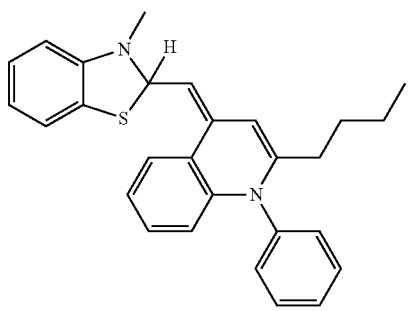

1

To a solution of (Z)-2-((2-butyl-1-phenylquinolin-4(1H)-ylidene)methyl)-3-methylbenzo[d]thiazol-3-ium iodide (350 mg, 0.636 mmol) in methanol (15 mL) was added sodium borohydride (96 mg, 2.54 mmol) slowly and the mixture was stirred at an ice-water bath temperature for 30 min. The reaction mixture was diluted with ethyl acetate (150 mL) and washed with water (2×50 mL). The separated organic layer was dried over $Na_2SO_4$ and filtered. After evaporation of the solvent, the crude product was purified by column chromatography over silica gel eluting with 2% ethyl acetate in hexane to give the desired product (1, 225 mg, 83% yield). TLC: $R_f$=0.45 (silica gel, 5% ethyl acetate in hexane).

Example 2

Synthesis of (Z)-2-((2-butyl-1-phenylquinolin-4(1H)-ylidene)methyl)-3-methyl-2-dueterio-3-hydrobenzo[d]thiazole (2)

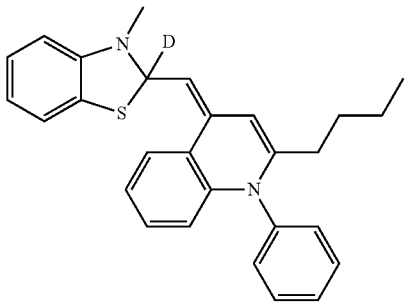

2

To a solution of (Z)-2-((2-butyl-1-phenylquinolin-4(1H)-ylidene)methyl)-3-methylbenzo[d]thiazol-3-ium iodide (100 mg, 0.18 mmol) in methanol (5 mL) was added sodium boroduetride (22 mg, 0.53 mmol) slowly and the mixture was stirred at an ice-water bath temperature for 30 min. The reaction mixture was diluted with ethyl acetate (50 mL) and washed with water (2×30 mL). The separated organic layer was dried over $Na_2SO_4$ and filtered. After evaporation of the solvent, the crude product was purified by column chromatography over silica gel eluting with 2% ethyl acetate in hexane to give the desired product (2, 50 mg, 65% yield). TLC: $R_f$=0.43 (silica gel, 5% ethyl acetate in hexane).

Example 3

Synthesis of (Z)-3-methyl-2-((1-propylquinolin-4(1H)-ylidene)methyl)-2,3-dihydrobenzo[d]thiazole (3)

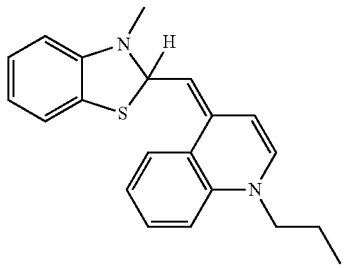

3

Compound 3 was prepared from (Z)-3-methyl-2-((1-propylquinolin-4(1H)-ylidene)methyl)benzo[d]thiazol-3-ium tosylate and sodium borohydride in a similar procedure as described in the above example of Compound 1.

Example 4

Synthesis of (Z)-2-((2-methoxy-1-phenylquinolin-4(1H)-ylidene)methyl)-3-methyl-2,3-dihydrobenzo[d]thiazole (4)

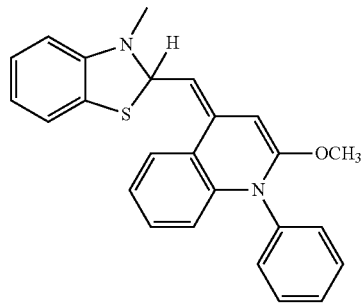

Compound 4 was prepared from (Z)-2-((2-methoxy-1-phenylquinolin-4(1H)-ylidene)methyl)-3-methylbenzo[d]thiazol-3-ium perchlorate and sodium borohydride in a similar procedure as described in the above example of Compound 1.

Example 5

Synthesis of (Z)—N1,N1-dimethyl-N3-(4-((3-methyl-2,3-dihydrobenzo[d]thiazol-2-yl)methylene)-1-phenyl-1,4-dihydroquinolin-2-yl)-N3-propylpropane-1,3-diamine (5)

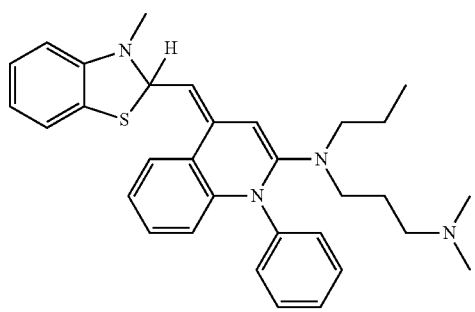

Compound 5 was prepared from (Z)-2-((2-((3-(dimethylamino)propyl)(propyl)amino)-1-phenylquinolin-4(1H)-ylidene)methyl)-3-methylbenzo[d]thiazol-3-ium chloride and sodium borohydride in a similar procedure as described in the above example of Compound 1.

Example 6

Synthesis of N-ethyl-N-(4-((Z)-4-((E)-3-(2-methyl-2,3-dihydrobenzo[d]thiazol-2-yl)allylidene)-1-phenyl-1,4-dihydroquinolin-2-yl)benzyl)ethanamine (6)

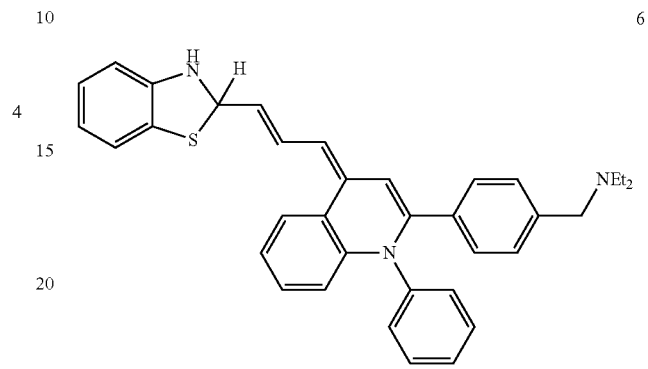

To a solution of 2-((1E,3Z)-3-(2-(4-((diethylamino)methyl)phenyl)-1-phenylquinolin-4(1H)-ylidene)prop-1-en-1-yl)-3-methylbenzo[d]thiazol-3-ium iodide (50 mg, 0.07 mmol) in methanol (5 mL) is added sodium borohydride (10 mg, 0.26 mmol) slowly and the mixture is stirred at an ice-water bath temperature for 30 min. The reaction mixture is diluted with ethyl acetate (50 mL) and washed with water (2×25 mL). The separated organic layer is dried over $Na_2SO_4$ and filtered. After evaporation of the solvent, the crude product is purified by column chromatography over silica gel eluting with 2% ethyl acetate in hexane to give the desired product (6).

Example 7

Synthesis of N-ethyl-N-(4-((Z)-1-methyl-4-((E)-3-(3-methyl-2,3-dihydrobenzo[d]thiazol-2-yl)allylidene)-1,4-dihydroquinolin-2-yl)benzyl)ethanamine (7)

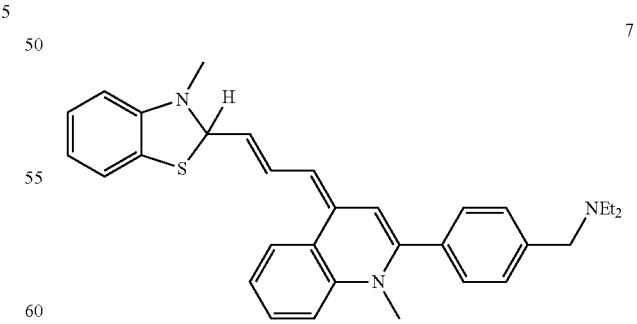

Compound 7 is prepared from 2-((1E,3Z)-3-(2-(4-((diethylamino)methyl)phenyl)-1-methylquinolin-4(1H)-ylidene)prop-1-en-1-yl)-3-methylbenzo[d]thiazol-3-ium iodide and sodium borohydride in a similar procedure as described in the above example of Compound 6.

II. Biological Application Examples of Reduced Dye Compounds (ROS Probes) Disclosed Herein

Example 8

Detection of Menadione-Induced ROS

Figure 2:
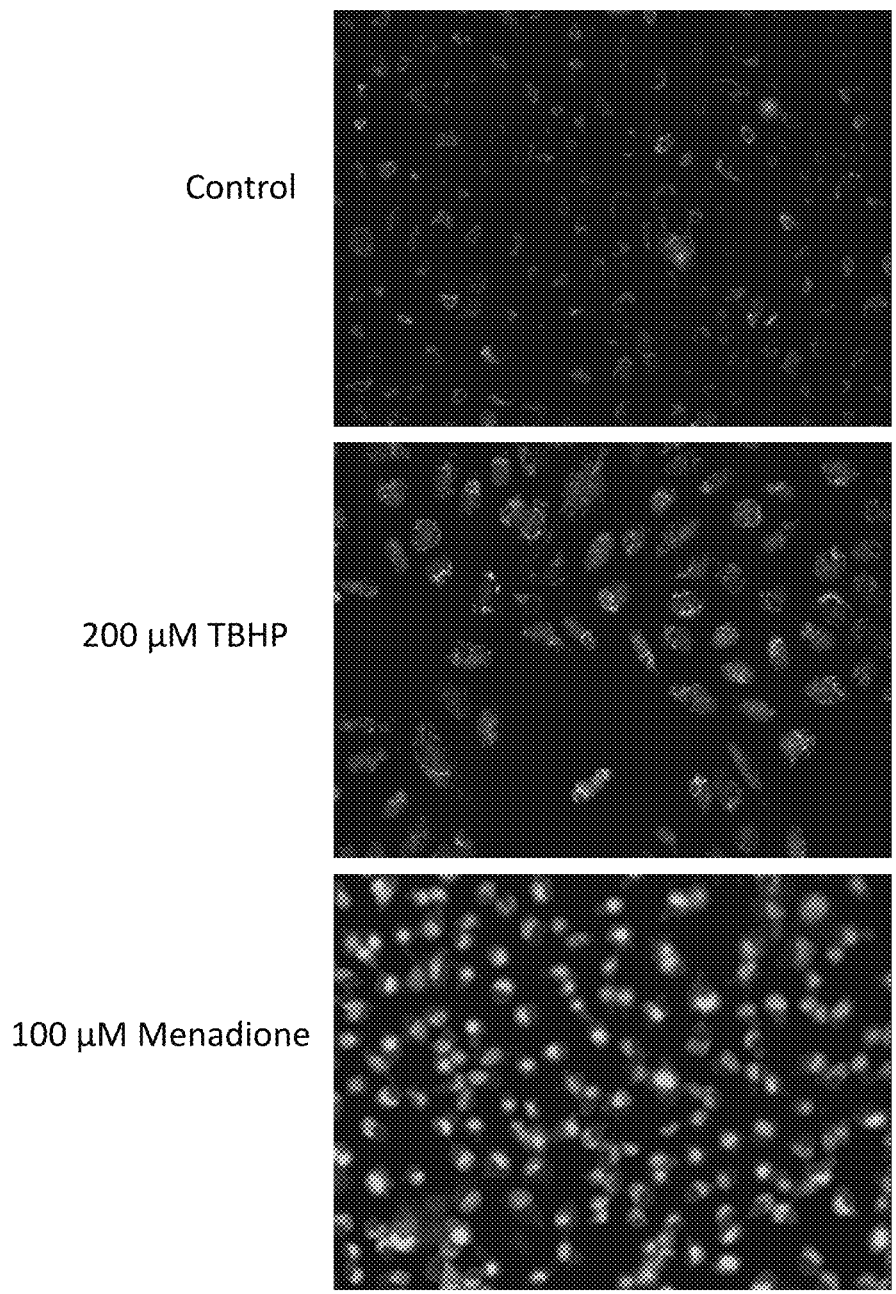
FIG. 2 shows detection of menadione-induced ROS formation in human osteosarcoma cells (U2-OS cells) using 5 μM Compound 1, according to certain embodiments of the present teachings.

Human osteosarcoma (U2-OS) cells were plated on Mat-Tek 30 mm dishes at a density of 200,000 cells/dish and incubated at 37° C. The cells were then treated with or without 200 μM tert-butyl hydroperoxide (TBHP, 2 hrs at 37° C.) or 100 μM menadione (1 hr at 37° C.). The cells were stained with 5 μM Compound 1 for the last 30 min of the drug incubation. The cells were washed 3× with phosphate buffered saline (PBS) and imaged on a Zeiss Axiovert inverted microscope using a 40× objective. An increase in the signal of Compound 1 was observed for all compounds tested, indicating an increase in oxidative stress in these cell models (see, FIG. 2).

Example 9

Detection of Oxidative Stress

Figure 3:
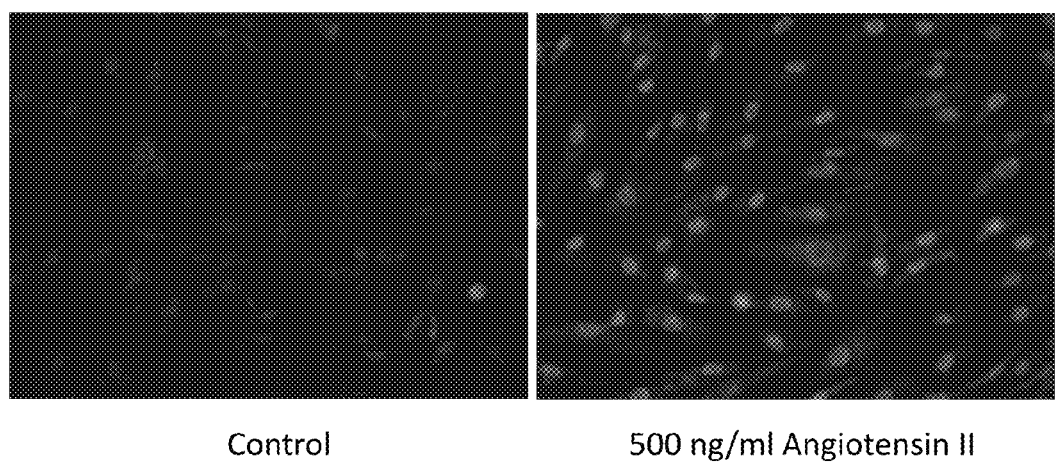
FIG. 3 shows detection of oxidative stress in human aortic smooth muscle (HASM) cells using 5 μM Compound 1, according to certain embodiments of the present teachings.

Human aortic smooth muscle (HASM) cells were plated on MatTek 30 mm dishes at a density of 150,000 cells/dish and incubated at 37° C. The cells were then treated with or without 500 ng/ml angiotensin-II for 4 hrs. The cells were stained with 5 μM Compound 1 for last 30 min of the drug incubation. The cells were washed 3× with PBS and imaged on a Zeiss Axiovert inverted microscope using a 40× objective. An increase in the signal of Compound 1 as observed for all compounds tested, indicating an increase in oxidative stress in these cell models (see, FIG. 3).

Example 10

Quantitative Detection of Menadione-Induced Oxidative Stress

Figure 4:
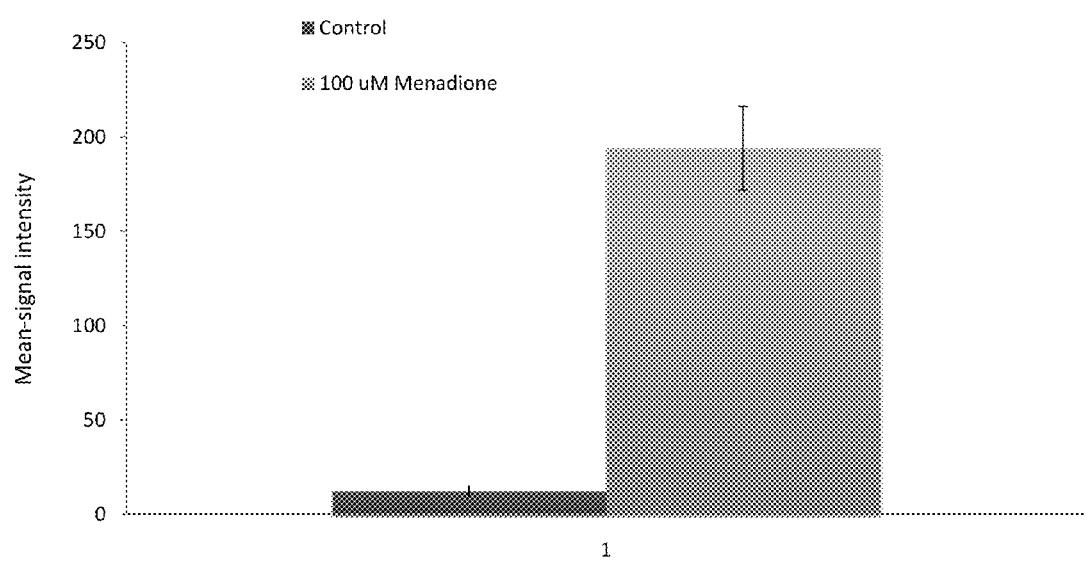
FIG. 4 shows quantitative detection of menadione-induced oxidative stress in bovine pulmonary arterial endothelial (BPAE) cells using Compound 1, according to certain embodiments of the present teachings.

Bovine pulmonary arterial endothelial (BPAE) cells were plated on 96-well plates at a density of 10,000 cells/well and incubated at 37° C. The cells were treated with 100 μM menadione for 1 hr at 37° C. The cells were stained with Compound 1 for 30 min at 37° C. The cells were then washed 3× with PBS and analyzed on a Thermo Fisher Cellomics® ArrayScan VTI (Thermo Fisher Scientific, Pittsburgh, Pa.). The mean signal intensities are plotted on the y-axis with control and treated samples on the x-axis (see, FIG. 4).

Example 11

Resistance to Formaldehyde Fixation and Detergent Permeabilization

Figure 5:
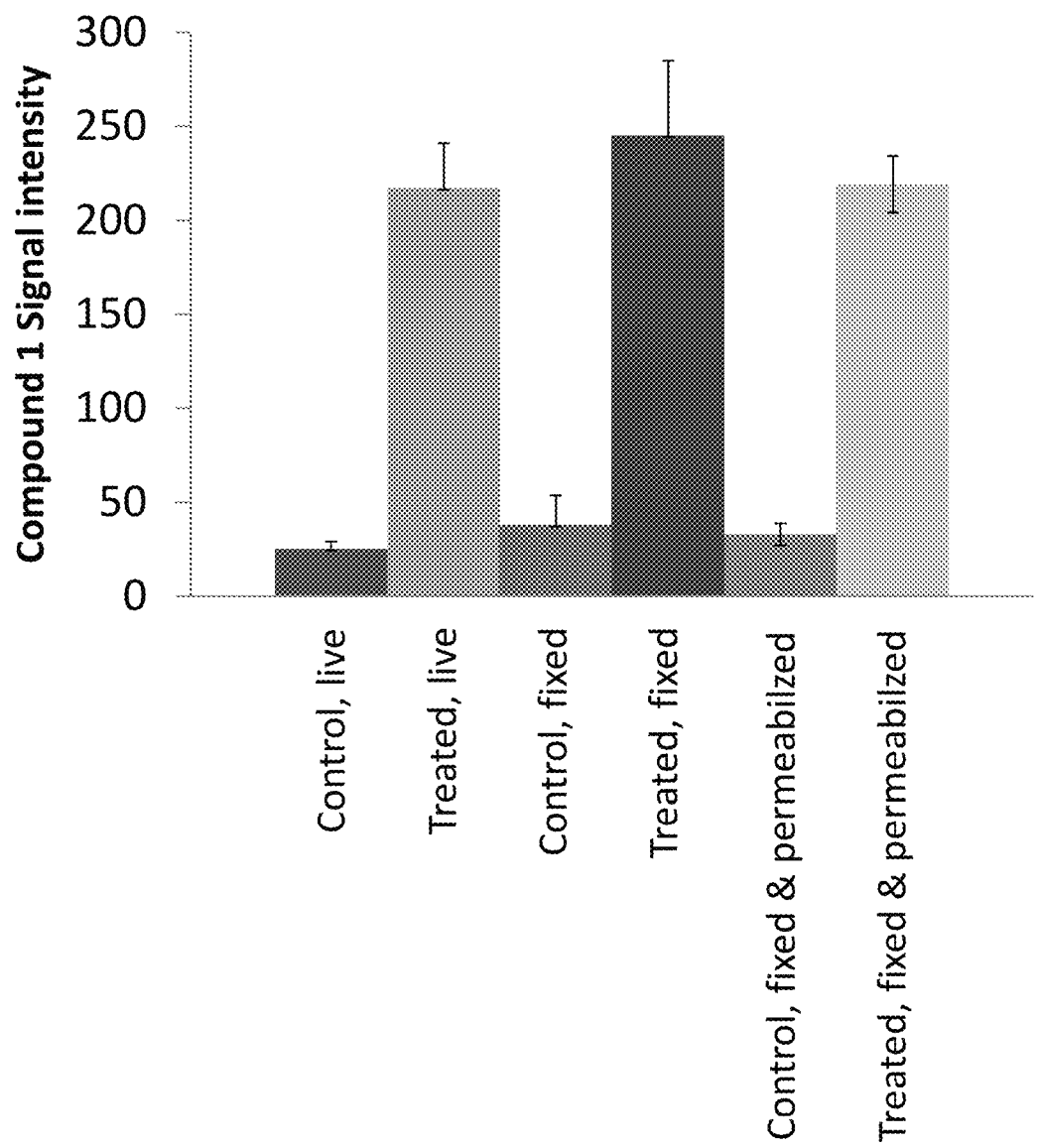
FIG. 5 shows resistance to formaldehyde fixation and detergent permeabilization in human osteosarcoma (U2-OS cells) using 5 μM Compound 1, according to certain embodiments of the present teachings.

Human osteosarcoma (U2-OS) cells were plated on a 96-well plate at a density of 7,500 cells/well and incubated overnight at 37° C. The cells were treated with or without 100 μM menadione for 1 hr at 37° C. The cells were then stained with 5 μM Compound 1 and Hoechst 33342 by adding the probes to complete media and incubating at 37° C. for 30 min. The cells were washed with PBS and imaged on a Thermo Fisher Cellomics ArrayScan® VTI, either live or 4% formaldehyde fixed or formaldehyde-fixed and permeabilized with 0.1% Triton X-100. Data shows that the Compound 1 signal is retained well after formaldehyde fixation and detergent permeabilization of cells (see, FIG. 5).

Example 12

Detection of Oxidative Stress Using Flow Cytometry

Figure 6A:
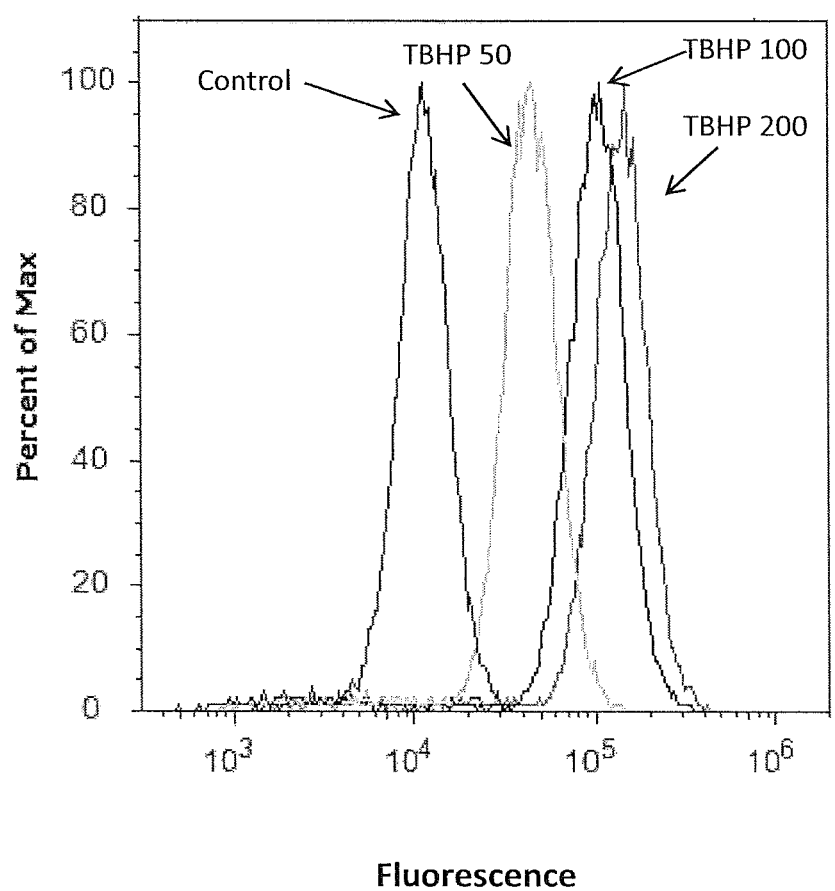
FIGS. 6A and 6B show detection of A) tert-butyl-hydroperoxide (TBHP)-induced or B) menadione-induced oxidative stress in Jurkat cells using 5 μM Compound 1, according to certain embodiments of the present teachings.
Figure 6B:
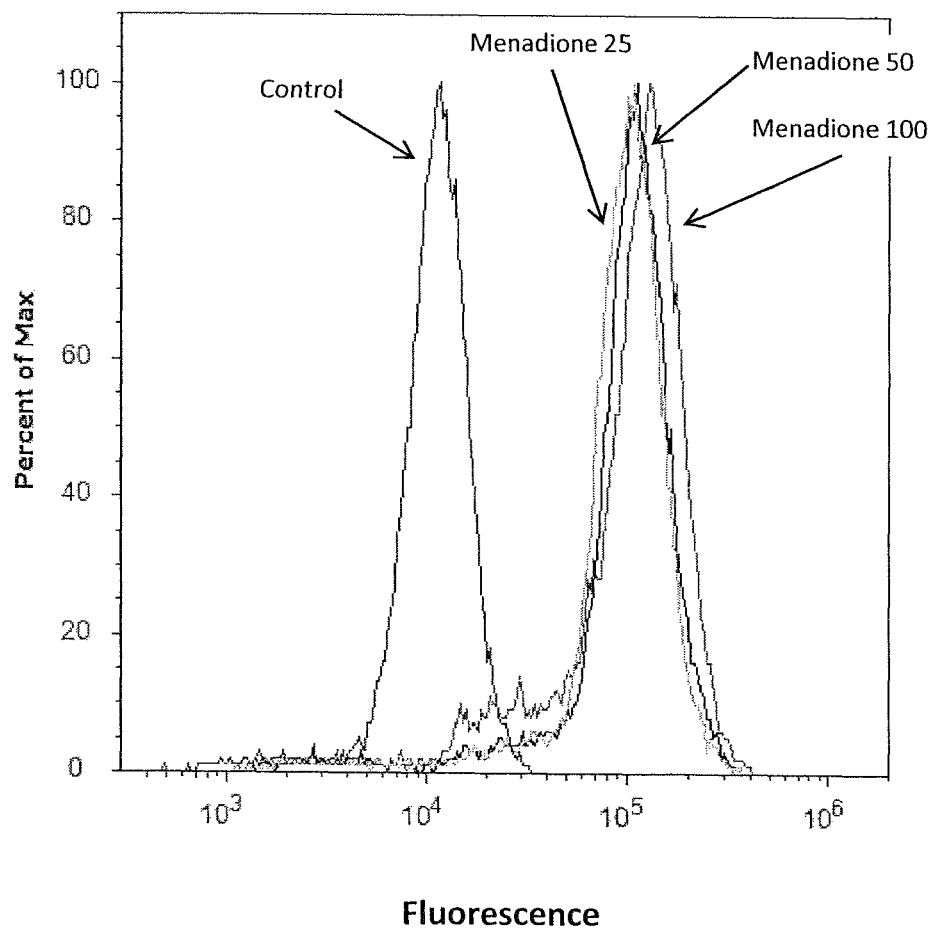

Jurkat cells were diluted in RPMI with 10% FBS to a density of $10^6$ cells/ml. Control cells were treated with vehicle control or DMSO, and sample cells were treated with different concentrations of menadione (25 μM, 50 μM, or 100 μM), or were treated with different concentrations of Tert-butyl hydroperoxide (TBHP) (50 μM, 100 μM, or 200 μM) for 60 min. Compound 1 was added to a final concentration of 5 μM for the last 30 minutes of drug incubation. The samples were acquired and analyzed on an Attune® Acoustic Focusing Cytometer. Compound 1 fluorescence was detected using the 488 nm laser and a 530/30 nm bandpass emission filter. A total of 20,000 events were collected using the standard 200 μl/minute collection rate. An increase in Compound 1 fluorescence intensity is observed in menadione and TBHP-treated cells compared to their controls (see, FIG. 6).

Example 13

Detection of THBP-Induced ROS

Figure 7:
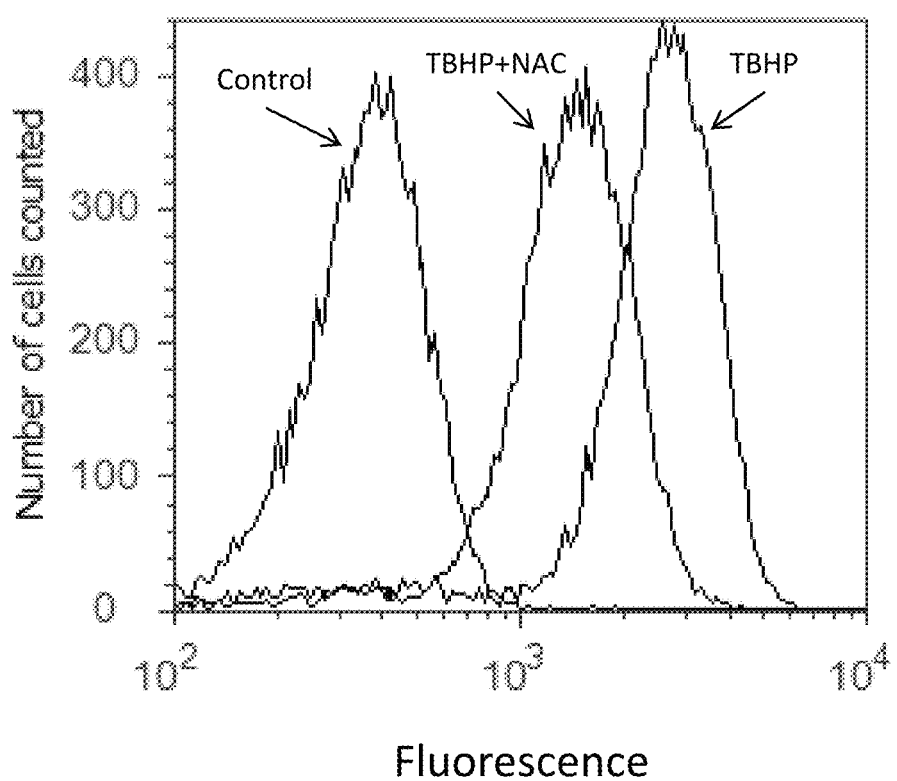
FIG. 7 shows the staining of Jurkat cells with Compound 1 is increased in cultures treated with tert-butyl-hydroperoxide (TBHP).

Jurkat cells were treated with phosphate buffered saline (FIG. 7, control), 200 μM tert-butyl-hydroperoxide (FIG. 7, TBHP), or 200 μM TBHP and 1 mM N-acetyl-L-cysteine (FIG. 7, TBHP+NAC), for one hour at 37° C., 5% $CO_2$ prior to incubation with 500 nM Compound 1. Cell samples were analyzed using a Becton Dickinson LSRII flow cytometer equipped with a 488 nm laser line and a 525/50 bandpass filter for collection of fluorescence emission of Compound 1. TBHP is a membrane-permeant pro-oxidant used extensively in a model of oxidative stress in different systems. Reduction in the oxidative stress response induced by TBHP has been attributed to the ability of the antioxidant, NAC, to replenish intracellular glutathione levels. This reduces levels of reactive oxygen species. Cells treated with TBHP alone demonstrated increased fluorescence emission from Compound 1 with a Mean Fluorescence Intensity (MFI) of 3944 compared to the MFI of control cells of 365. Cells treated with both TBHP and NAC demonstrated decreased MFI of Compound 1 fluorescence (MFI=2768) compared to cells treated with TBHP. This demonstrates a decrease in reactive oxygen species within the cells as a result of the enhanced antioxidant capacity of the cells due to increased glutathione levels.

Example 14

Detection of ROS does not Require a Post-Staining Wash Step

Figure 8:
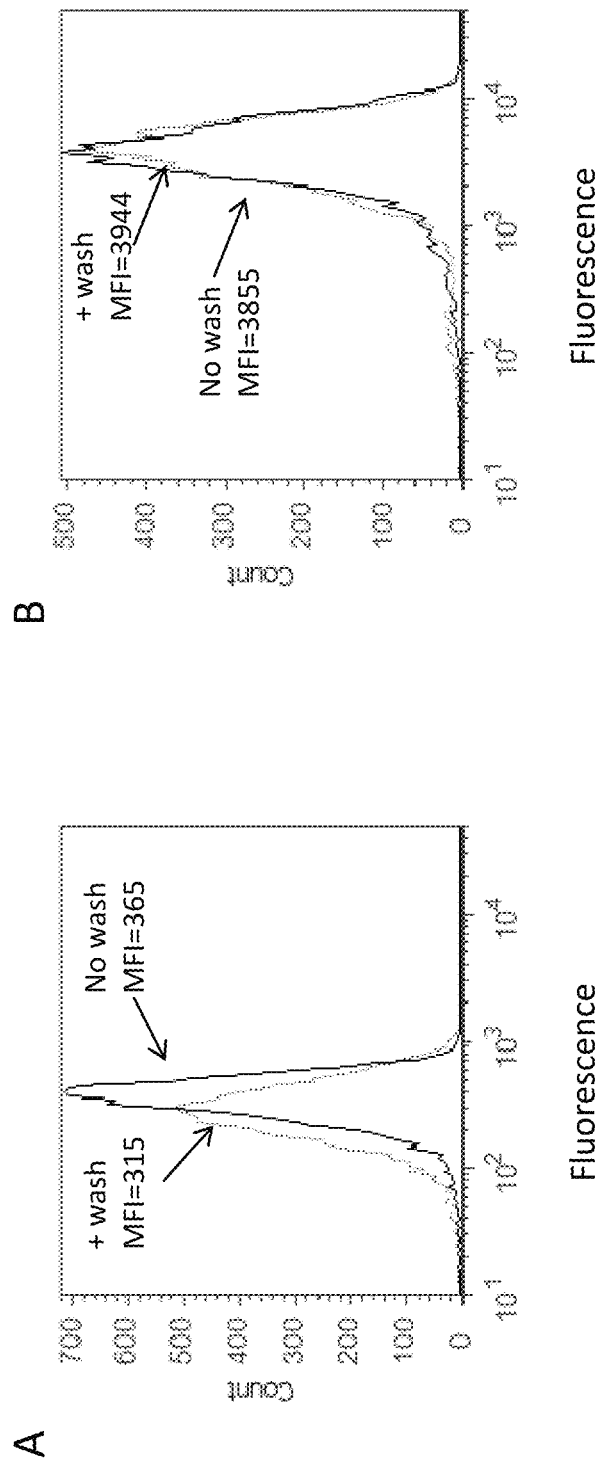
FIG. 8 shows dose-dependent ROS generation by TBHP in Jurkat cells using Compound 1 does not require a post-staining washing step for visualization using Jurkat cells (panel A: control, panel B: 200 µM TBHP treatment).

Jurkat cells (T-cell leukemia, human) were treated with phosphate buffered saline (control; FIG. 8, panel A) or 200 μM tert-butyl-hydroperoxide (TBHP; FIG. 8, panel B) for one hour at 37° C., 5% $CO_2$ prior to incubation with 500 nM Compound 1. Cell samples were directly analyzed on a Becton Dickinson LSRII flow cytometer equipped with a 488 nm laser line and a 525/50 bandpass filter for collection of fluorescence emission of Compound 1. Histogram overlays show cells analyzed immediately following 30 minutes incubation with Compound 1 (FIG. 8) compared to samples analyzed following three-3 mL wash steps (FIG. 8). The median fluorescence intensity (MFI) of Compound 1 fluorescence was not significantly different from that of washed cells. The signal to noise ratio (or fold change in TBHP-treated cells as compared to control cells) in the no-wash samples was similar to the signal to noise ratio in the samples that were washed three times, 9.1 and 10.4, respectively, for the no-wash and the washed sample. This indicates that Compound 1 may be used without a wash step; unlike other prior art ROS probes that require such a wash step.

Example 15

Detection of ROS in Complete Media Vs. Protein-Containing Buffer

Figure 9:
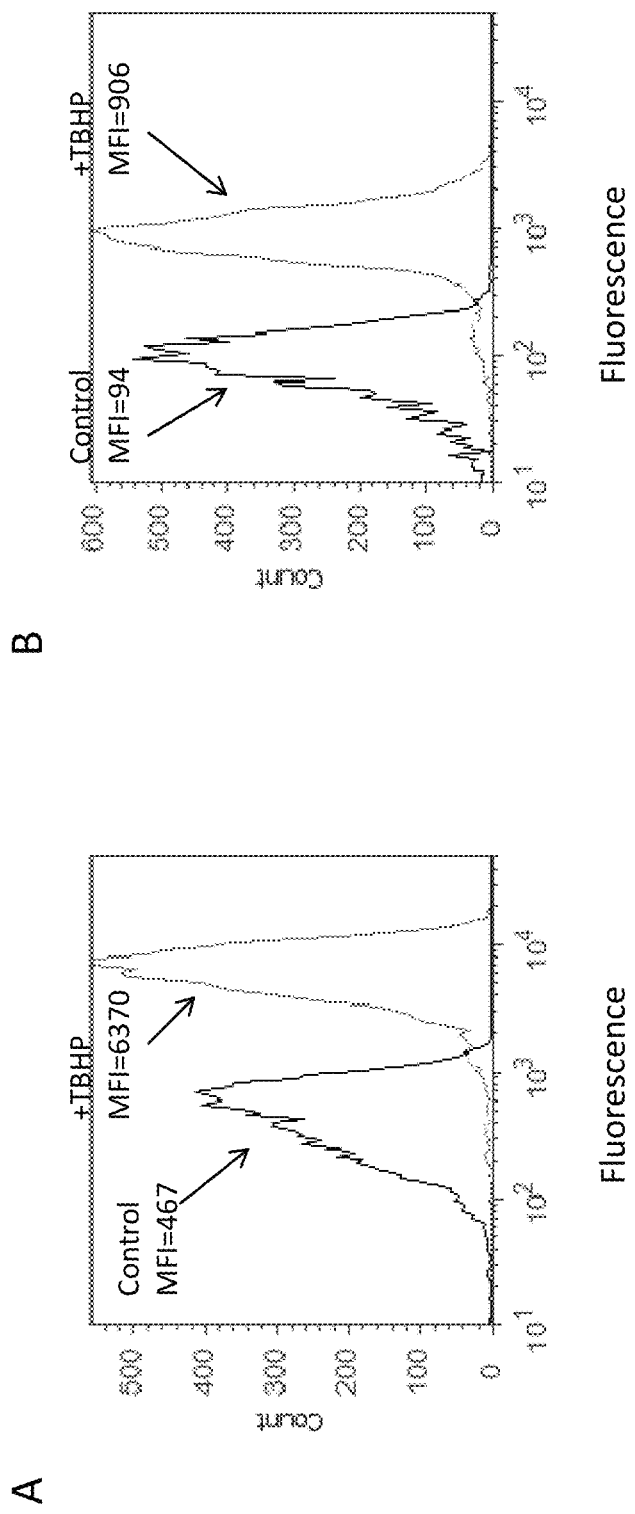
FIG. 9 shows dose-dependent ROS generation by TBHP in Jurkat cells using Compound 1 in complete media (panel A) versus protein-containing buffer (panel B).

Jurkat cells (T-cell leukemia, human) were resuspended in complete medium (RPMI 1640 medium, GIBCO (Life Technologies, Carlsbad, Calif.), supplemented with 10% Fetal Bovine Serum, FBS) or phosphate buffered saline supplemented with 1% bovine serum albumin (BSA). Cells in both complete medium (FIG. 9, panel A) and buffered saline+1% BSA (FIG. 9, panel B) were treated with diluents control, phosphate buffered saline alone (FIG. 9, control) or 400 μM tert-butyl-hydroperoxide (FIG. 9, TBHP) for 30 minutes at 37° C., 5% $CO_2$ prior to staining with 500 nM Compound 1. Cell samples were analyzed on a BD LSRII flow cytometer equipped with a 488 nm laser line and a 525/50 bandpass filter for collection of fluorescence emission of Compound 1. The median fluorescent intensity (MFI) of Compound 1 fluorescence in control cells (FIG. 9, panel A) and the MFI of Compound 1 fluorescence in TBHP-treated cells (FIG. 9, panel B) stained in complete media (FIG. 9, panel A) were increased compared to samples stained in protein-containing buffer (FIG. 9, panel B). As a consequence, the signal to noise ratio (or fold change in TBHP-treated cells as compared to control cells) in the samples stained in complete media (FIG. 9, panel A) is greater (13.6) than the signal to noise ratio in the samples stained in protein-containing buffer (9.6). This indicates that Compound 1 may be used to stain cells in complete medium, offering the user a significant advantage over existing prior art ROS detection reagents that require staining in a protein-free buffer.

III. Biological Application Examples of Reduced Dye Compounds (ROS Probes) Disclosed Herein In addition to the applications described above, the reduced dye compounds (ROS probes) disclosed herein and compositions containing those dyes may be used in vitro as diagnostic tools to detect or quantify ROS in a variety of samples. Further, the reduced dye compounds (ROS probes) disclosed herein and compositions containing those dyes may be used in vivo to detect a variety of diseases and disorders or markers for diseases and disorders characterized by production of overproduction of ROS, as well as in positron emission tomography (PET) as contrast agents, imaging of biomolecules, and photoacoustic imaging.

Example 16

Imaging of ROS Production In Vivo

The ability of the reduced dye compounds (ROS probes) disclosed herein to image ROS production in vivo generated by activated macrophages and neutrophils in an LPS model of acute inflammation is evaluated. Briefly, mice are divided into three groups: Group I is given an intraperitoneal (i.p.) injection of LPS (1 mg in 400 μL saline); Group II is given an i.p. injection of saline (400 μL); and Group III is untreated. After 6 h, the mice are anesthetized, their abdominal fur is removed, and the LPS- and saline-treated mice are injected i.p. with a ROS probe (~5 nM in 50 μL methanol). The mice are imaged as triplets, one from each group, using an in vivo imaging system, such as the Kodak In-Vivo Imaging System FX (Kodak Molecular Imaging Systems, New Haven, Conn.).

The invention claimed is:
1. A reduced dye compound having structural formula (II):

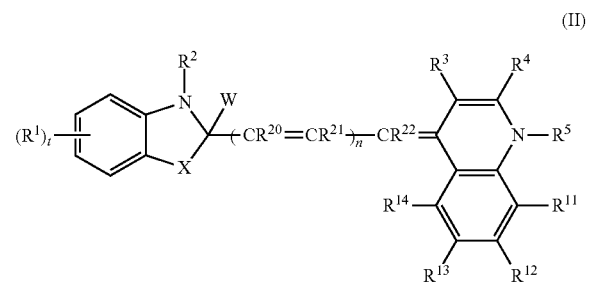

wherein
each $R^1$ is H;
t is 4;
$R^2$ is a substituted or unsubstituted $C_1$-$C_6$ alkyl;
$R^5$ is selected from the group consisting of $C_1$-$C_6$ alkyl, $C_1$-$C_6$ alkenyl, $C_1$-$C_6$ polyalkenyl, $C_1$-$C_6$ alkynyl, $C_1$-$C_6$ polyalkynyl and an OMEGA;
$R^3$, $R^4$, $R^{11}$, $R^{12}$, $R^{13}$ and $R^{14}$ are each independently selected from the group consisting of H, halogen, $C_1$-$C_6$ alkyl, $C_1$-$C_6$ alkenyl, $C_1$-$C_6$ polyalkenyl, $C_1$-$C_6$ alkynyl, $C_1$-$C_6$ polyalkynyl, —$OR^8$, —$SR^8$, —($NR^8R^9$), —$OSO_2R^{19}$, and an OMEGA, wherein $R^8$ and $R^9$, which may be the same or different, are independently selected from the group consisting of H and $C_1$-$C_6$ alkyl;
$R^{19}$ is a $C_1$-$C_6$ alkyl, $C_1$-$C_6$ perfluoroalkyl, or aryl;
OMEGA is a substituted or unsubstituted phenyl, wherein the OMEGA is attached at $R^3$, $R^4$, $R^5$, $R^{11}$, $R^{12}$, $R^{13}$, or $R^{14}$ by a single bond,
wherein when more than one of $R^3$, $R^4$, $R^5$, $R^{11}$, $R^{12}$, $R^{13}$, and $R^{14}$ is an OMEGA, each OMEGA is optionally the same or different, and
wherein one or two of $R^3$, $R^4$, $R^5$, $R^6$, $R^7$, $R^{11}$, $R^{12}$, $R^{13}$ and $R^{14}$ is an OMEGA;
X is O, S, Se, $NR^{15}$ or $CR^{16}R^{17}$;
$R^{16}$ and $R^{17}$, which may be the same or different, are independently selected from the group consisting of H and $C_1$-$C_6$ alkyl;
$R^{15}$ is H or $C_1$-$C_6$ alkyl;
$R^{20}$, $R^{21}$ and $R^{22}$ are independently H, $C_1$-$C_6$ alkyl, $C_3$-$C_{10}$ cycloalkyl, aryl or heteroaryl;
W is H or D in either the R or S configuration; and
n is 0, 1, 2, or 3.
2. The compound according to claim 1, wherein:
$R^2$ is methyl or ethyl;
$R^4$ is $C_1$-$C_6$ alkyl;
$R^5$ is phenyl;
X is S; and
n is 0.

3. A reduced dye compound selected from the group consisting of:
 (Z)-2-((2-butyl-1-phenylquinolin-4(1H)-ylidene)methyl)-3-methyl-2,3-dihydrobenzo[d]thiazole;
 (Z)-2-((2-butyl-1-phenylquinolin-4(1H)-ylidene)methyl)-3-methyl-2-dueterio-3-hydrobenzo[d]thiazole;
 (Z)-3-methyl-2-((1-propylquinolin-4(1H)-ylidene)methyl)-2,3-dihydrobenzo[d]thiazole;
 (Z)-2-((2-methoxy-1-phenylquinolin-4(1H)-ylidene)methyl)-3-methyl-2,3-dihydrobenzo[d]thiazole;
 (Z)—N1,N1-dimethyl-N3-(4-((3-methyl-2,3-dihydrobenzo[d]thiazol-2-yl)methylene)-1-phenyl-1,4-dihydroquinolin-2-yl)-N3-propylpropane-1,3-diamine;
 N-ethyl-N-(4-((Z)-4-((E)-3-(2-methyl-2,3-dihydrobenzo[d]thiazol-2-yl)allylidene)-1-phenyl-1,4-dihydroquinolin-2-yl)benzyl)ethanamine; and
 N-ethyl-N-(4-((Z)-1-methyl-4-((E)-3-(3-methyl-2,3-dihydrobenzo[d]thiazol-2-yl)allylidene)-1,4-dihydroquinolin-2-yl)benzyl)ethanamine.

4. A composition for the detection of reactive oxygen species (ROS), the composition comprising:
 a) one or more reduced dyes; and
 b) a carrier,
 wherein said reduced dyes are compounds according to claim 1 and are present in an amount effective to detect the presence of ROS upon reaction with ROS.

5. The composition according to claim 4, wherein the composition is suitable for in vitro applications.

6. The composition according to claim 4, wherein the composition is suitable for in vivo applications.

7. A method of detecting reactive oxygen species (ROS) in a sample, the method comprising the steps of:
 a) contacting the sample with an effective amount of one or more of the reduced dye compounds according to claim 1; and
 b) determining if the reduced dye compound has been oxidized.

8. A method of detecting reactive oxygen species (ROS) in a sample, the method comprising the steps of:
 a) contacting the sample with an effective amount of the composition according to claim 4; and
 b) determining if the reduced dye compound has been oxidized.

9. The method according to claim 7, wherein the sample comprises cells, tissues, biological fluids, or combinations thereof.

10. The method according to claim 7, wherein oxidation of the reduced dye compound is detected by fluorescence spectroscopy.

11. The method according to claim 7, wherein oxidation of the reduced dye compound is detected by fluorescence microscopy.

12. The method according to claim 7, wherein oxidation of the reduced dye compound is detected by confocal laser scanning fluorescence microscopy.

13. The method according to claim 7, wherein oxidation of the reduced dye compound is detected by total internal reflection fluorescence microscopy.

14. The method according to claim 7, wherein the detection of the reactive oxygen species (ROS) is used to diagnose a disease or disorder selected from the group consisting of carotid artery injuries, atherosclerosis, hypertension, cancers, diseases and disorders characterized by inflammation, radiation-induced late normal tissue damage; tissue damages due to chemotherapy, reperfusion after ischemia, or transplantation; diabetes, such as type 1 diabetes (T1D), neurodegenerative diseases, such as Alzheimer's disease, Parkinson's disease, amyotrophic lateral sclerosis (ALS), and Huntington's disease; cerebrovascular disease, cystic fibrosis, chronic kidney disease, cardiovascular disease, preeclampsia, ophthalamic diseases, and combinations thereof.

15. A kit for detecting reactive oxygen species (ROS) in a sample, the kit comprising:
 a) one or more reduced dye compounds according to claim 1; and
 b) one or more containers.

16. A kit for detecting reactive oxygen species (ROS) in a sample, the kit comprising:
 a) the composition according to claim 4; and
 b) one or more containers.

17. The kit according to claim 15, wherein the kit further comprises instructions for performing an assay for detecting one or more reactive oxygen species (ROS) comprising the steps of:
 a) contacting the sample with an effective amount of one or more of the reduced dye compounds;
 b) measuring fluorescence intensity of the one or more dye compounds; and
 c) determining if the reduced dye compound has been oxidized;
 wherein an increase in fluorescence intensity is indicative of the presence of ROS in the sample.

18. The kit according to claim 17, wherein the assay is performed in vivo or in vitro.

19. A process for preparing a reduced dye compound according to claim 1, the process comprising:
 a) reacting a cyanine compound having structural formula (IV)

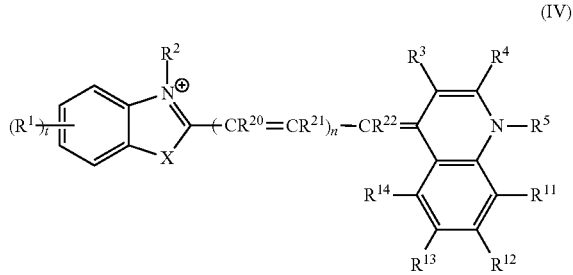

with a reducing agent, wherein:
 X, $R^1$, $R^2$, $R^3$, $R^4$, $R^5$, $R^{11}$, $R^{12}$, $R^{13}$, $R^{14}$, $R^{20}$, $R^{21}$, $R^{22}$, n, and t are as defined in claim 2.

* * * * *

UNITED STATES PATENT AND TRADEMARK OFFICE
CERTIFICATE OF CORRECTION

PATENT NO. : 9,518,981 B2  
APPLICATION NO. : 14/384843  
DATED : December 13, 2016  
INVENTOR(S) : Yi-Zhen Hu et al.

Page 1 of 1

It is certified that error appears in the above-identified patent and that said Letters Patent is hereby corrected as shown below:

In the Claims

In Column 34, Line 57, the claim reference numeral "2", should read --1--.

Signed and Sealed this
Twenty-fifth Day of April, 2017

Michelle K. Lee
*Director of the United States Patent and Trademark Office*